United States Patent
Cheng et al.

(10) Patent No.: US 7,956,238 B2
(45) Date of Patent: Jun. 7, 2011

(54) PORCINE PANCREATIC AMYLASE GENE PROMOTER AND TRANSGENIC PIGS EXPRESSING HETEROLOGOUS DIGESTIVE ENZYMES

(75) Inventors: Teng-Kuei Winston Cheng, Taipei (TW); Shinn-Chih Wu, Taipei (TW); Chi-Chen Hsu, Taipei (TW); Yu-Sheng Lin, Taipei (TW); Chih-Jen Lin, Taipei (TW); Kuo-Joan Cheng, Hisn Chu (TW); Jih-Tay Hsu, Taipei (TW)

(73) Assignee: National Taiwan University (An University of Taiwan, R.O.C.), Taipei (TW)

( * ) Notice: Subject to any disclaimer, the term of this patent is extended or adjusted under 35 U.S.C. 154(b) by 794 days.

(21) Appl. No.: 11/438,979

(22) Filed: May 23, 2006

(65) Prior Publication Data

US 2007/0277253 A1 Nov. 29, 2007

(51) Int. Cl.
*A01K 67/027* (2006.01)
*C12N 15/52* (2006.01)
*C12N 15/63* (2006.01)
*C12N 15/85* (2006.01)
*C07H 21/04* (2006.01)

(52) U.S. Cl. ............... 800/17; 800/13; 800/21; 800/25; 536/24.1; 435/320.1

(58) Field of Classification Search .................. 800/13, 800/17, 21, 25; 536/24.1; 435/320.1
See application file for complete search history.

(56) References Cited

OTHER PUBLICATIONS

Hall et al. (1993) Bio/Technology, vol. 11, 376-379.*
Ali et al. (1995) Prog. Biotechnol., vol. 10, 279-293.*
Zhang et al. (1999) Arch. Biochem. Biophys, vol. 367 (2), 317-321.*

* cited by examiner

*Primary Examiner* — Anne Marie S Wehbe
(74) *Attorney, Agent, or Firm* — Occhiuti Rohlicek & Tsao LLP

(57) ABSTRACT

The present invention relates to a novel promoter and its use in driving expression of foreign genes in transgenic animals (especially pigs). Accordingly, the present invention provides a method for producing transgenic animals harboring heterologous genes regulated by the promoter of the present invention.

11 Claims, 10 Drawing Sheets

SEQUENCE LISTING

<160> NUMBER OF SEQ ID NOS: 32

<210> SEQ ID NO 1
<211> LENGTH: 2533
<212> TYPE: DNA
<213> ORGANISM: Sus scrofa

<400> SEQUENCE: 1

```
ctgacataag ctgaaccaat gccttgcata atacctgcaa tttagagtct ataagtaaaa      60
accacttatt gatcacatga gccatcgtgc tgttttttg ctaggaatat taactatgaa      120
atctgctctt aataaggttt atccagaatg acagtcatgt aaatccttat tttttataac     180
attaatccaa tatcacttaa taacaacccg gaggttaaaa cctgccatac agaggagtac     240
ataactatgg ctgggaatat caatataagt ttcataaagg tatttttcca actgcatatg     300
aaagtaggag tagttactag ctattgaagg gtgatacaag aaagaagaaa agccctggaa     360
agtcatgaaa gaataaaatt gcttgtcaaa tacgcaaaat gtttattttt tgcgggagat     420
ggatattggg gactctgcac ttgtgttccg cccctctaac aatttgaaat attgaactcc     480
taactcccaa tggtatgcga ttaggctgtg gggtctttgg gaacaactta ggtcaaagtg     540
acatcatgag agtggaggcc ccatgatggg ttagtgtcct tgtacgaaga gaaagagaat     600
caggatctct gagctccaca ctccgtgagg atacaagaag cttgctgtct gtgaacatgg     660
aatgggcttt cgcaagaca ctggagctgc tgatagtgta gtcttgggtt tcccagcctc      720
tagaaatgtg agaaagaaat atttgtgcta agccatccag cctatatggc attcttgtta     780
```

```
cagcagctgg aactgaatga gaaaaatagg acacggagta tgttcacgat gtgggctgga      840
ggagggaccg aaggagagtg ttgggattca cagagtgctc tcggacccc tccacaaagc      900 tagtacttcc tcactttcc tcatcttagt aaatggtgtc atcagatacc tgtttcctca      960 attttctct ttcccccagt cttcggtgct aatctatcga taaaccgatt gcttcgccac     1020
ctctgagata tattctatca gggccctaga gcagccactt tcctcttcg tggaccacta     1080 caaaagccta cctgatctct tggccccag tcgtgtcctc ctataatccg gttttcaca     1140 gcagagcaag aatggttttc ttggaaagga aatcagaatc tcttcactca tcttcttca     1200 gcctcaaaag ccctctcttt ccttatgttc tacaaggttc tacatgatct ggcctacctc     1260
tctgatttca tctcattta ctcttcctt tgtcactcac acatgtttag ctgcactgat     1320
gttgaaagtt tgttcagtgt cacttgagta tcccacggtt gttcctacct tgggcttttg     1380
ctattgcact ttcctctatg gagactgctt ttcctctgat cttcaaataa gtgggtcctt     1440
ctactccttc cagttctggc tgacaatcac tccctctgaa acagctttcc tgactatttc     1500
cagtctaaaa tatcctgaaa aattcagtcc ttttcccttt aactgcaccg tgggttcatg     1560
ctagttctca ctgctctctt taacttagta tcgttgttgt tatcattcca tcttgctata     1620
ttttccttac cttcccctag aatgtaggct gagaacaaga gtcttgtctg tcttgttcat     1680
ccttgtatcc tgagtatcat gccggcattt agcaaaagca ctcggccact acctgttgga     1740
tgaatggatt aggttttcc cacctgtacg gttatgtctt tactaggatt tcttgtacct     1800
tacgaaggaa aatagatgtg gattcattaa cttagtgttt tagcacatat aagggacttt     1860
ttgctagaag gagaaaaaaa aaagtccatt cttcctgct acagccagtg cattttcaca     1920
tgcgttaatg taagcgtggg gaaaaaaaaa tctgacacct aaagtcgtgg tcatttcact     1980
tccggataac ttcctaaatc ttagtggaga atctcaagta tctaacaact ggggtaggag     2040
gtaccaactg aactgagttg aataacatgt gtcttcttac aatggaaaca ttgcacgtgt     2100
ttacagacag ttagggcacc attgtgactg tgaattcagt tggctctaat tccgcctctg     2160
tcagtgaagg acttcagaaa taaaatctaa tcctacctaa acaatacatg attaagacct     2220
ttctgtagat aacatgccag atgtttcaaa acttgctgtt ccctcagtaa ggaaaacatt     2280
gtctgagaag gtcatttaga tagtattcct gggagatttt cgggatgttc ctcacctgtt     2340
tagtgtaatt atcaatagtt attttggag tatgcattca cggtttgtgc tctaagtatt     2400
tattcatgtc aatatttgct ttgtaaaata tgcttcttgc aggattataa atacttgccg     2460
ggaagaccgt tgacaacctc agagcaaaat gaagttgttt ctgctgcttt cagccattgg     2520
gttctgctgg gcc                                                         2533

<210> SEQ ID NO 2
<211> LENGTH: 3990
<212> TYPE: DNA
<213> ORGANISM: Artificial
<220> FEATURE:
<221> NAME/KEY: CDS
<222> LOCATION: (2540)..(3739)
<223> OTHER INFORMATION: expression cassette

<400> SEQUENCE: 2
ctgacataag ctgaaccaat gccttgcata ataccctgcaa tttagagtct ataagtaaaa       60
accacttatt gatcacatga gccatcgtgc tgttttttg ctaggaatat taactatgaa      120
atctgctctt aataaggttt atccagaatg acagtcatgt aaatccttat tttttataac      180
attaatccaa tatcacttaa taacaacccg gaggttaaaa cctgccatac agaggagtac      240
```

```
ataactatgg ctgggaatat caatataagt ttcataaagg tattttttcca actgcatatg      300 aaagtaggag tagttactag ctattgaagg gtgatacaag aaagaagaaa agccctggaa      360
agtcatgaaa gaataaaatt gcttgtcaaa tacgcaaaat gtttatttttt tgcgggagat     420 ggatattggg gactctgcac ttgtgttccg cccctctaac aatttgaaat attgaactcc     480
taactcccaa tggtatgcga ttaggctgtg gggtctttgg gaacaactta ggtcaaagtg     540
acatcatgag agtggaggcc ccatgatggg ttagtgtcct tgtacgaaga gaaagagaat     600
caggatctct gagctccaca ctccgtgagg atacaagaag cttgctgtct gtgaacatgg     660
aatgggcttt cgcaagaca ctggagctgc tgatagtgta gtcttgggtt tcccagcctc      720
tagaaatgtg agaaagaaat atttgtgcta agccatccag cctatatggc attcttgtta     780
cagcagctgg aactgaatga gaaaaatagg acacggagta tgttcacgat gtgggctgga    840
ggagggaccg aaggagagtg ttgggattca cagagtgctc tcggacccccc tccacaaagc    900 tagtacttcc tcactttttcc tcatcttagt aaatggtgtc atcagatacc tgtttcctca     960
atttttctct ttcccccagt cttcggtgct aatctatcga taaaccgatt gcttcgccac    1020
ctctgagata tattctatca gggccctaga gcagccactt tcctctttcg tggaccacta    1080
caaaagccta cctgatctct tggcccccag tcgtgtcctc ctataatccg ttttttcaca    1140
gcagagcaag aatggttttc ttggaaagga aatcagaatc tcttcactca tcttctttca    1200
gcctcaaaag ccctctcttt ccttatgttc tacaaggttc tacatgatct ggcctacctc    1260
tctgatttca tctcattttta ctcttccctt tgtcactcac acatgtttag ctgcactgat    1320
gttgaaagtt tgttcagtgt cacttgagta tcccacggtt gttcctacct tgggcttttg    1380
ctattgcact ttcctctatg gagactgctt ttcctctgat cttcaaataa gtgggtcctt    1440
ctactccttc cagttctggc tgacaatcac tccctctgaa acagcttttcc tgactatttc    1500 cagtctaaaa tatcctgaaa aattcagtcc ttttcccttt aactgcaccg tgggttcatg    1560
ctagttctca ctgctctctt taacttagta tcgttgttgt tatcattcca tcttgctata    1620 tttttccttac cttcccctag aatgtaggct gagaacaaga gtcttgtctg tcttgttcat    1680
ccttgtatcc tgagtatcat gccggcattt agcaaaagca ctcggccact acctgttgga    1740
tgaatggatt aggttttttcc cacctgtacg gttatgtctt tactaggatt tcttgtacct    1800
tacgaaggaa aatagatgtg gattcattaa cttagtgttt tagcacatat aagggacttt    1860
ttgctagaag gagaaaaaaa aaagtccatt cttttcctgct acagccagtg cattttcaca    1920
tgcgttaatg taagcgtggg gaaaaaaaa tctgacacct aaagtcgtgg tcatttcact    1980
tccggataac ttcctaaatc ttagtggaga atctcaagta tctaacaact ggggtaggag    2040
gtaccaactg aactgagttg aataacatgt gtcttcttac aatggaaaca ttgcacgtgt    2100
ttacagacag ttagggcacc attgtgactg tgaattcagt tggctctaat tccgcctctg    2160
tcagtgaagg acttcagaaa taaaatctaa tcctacctaa acaatacatg attaagacct    2220
ttctgtagat aacatgccag atgtttcaaa acttgctgtt ccctcagtaa ggaaaacatt    2280
gtctgagaag gtcatttaga tagtattcct gggagatttt cgggatgttc ctcacctgtt    2340
tagtgtaatt atcaatagtt attttttggag tatgcattca cggtttgtgc tctaagtatt    2400
tattcatgtc aatatttgct ttgtaaaata tgcttcttgc aggattataa atacttgccg    2460
ggaagaccgt tgacaacctc agagcaaaat gaagttgttt ctgctgcttt cagccattgg    2520
gttctgctgg gccggatcc att atg aaa ccc gaa cca aca gaa gtt act aca    2572
                        Ile Met Lys Pro Glu Pro Thr Glu Val Thr Thr
                         1               5                  10
```

-continued

| | | | | | | | | | | | | | | | | |
|---|---|---|---|---|---|---|---|---|---|---|---|---|---|---|---|---|
| gaa | gct | aca | aca | gaa | gct | act | gaa | tca | acg | gaa | act | acc | gtt | cca | atc | 2620 |
| Glu | Ala | Thr | Thr | Glu | Ala | Thr | Glu | Ser | Thr | Glu | Thr | Thr | Val | Pro | Ile | |
| | | | 15 | | | | 20 | | | | | 25 | | | | |

| | | | | | | | | | | | | | | | | |
|---|---|---|---|---|---|---|---|---|---|---|---|---|---|---|---|---|
| aat | cca | tct | act | gga | att | cgt | gat | att | tct | tct | aaa | gaa | tta | att | aaa | 2668 |
| Asn | Pro | Ser | Thr | Gly | Ile | Arg | Asp | Ile | Ser | Ser | Lys | Glu | Leu | Ile | Lys | |
| | | 30 | | | | | 35 | | | | 40 | | | | | |

| | | | | | | | | | | | | | | | | |
|---|---|---|---|---|---|---|---|---|---|---|---|---|---|---|---|---|
| gag | atg | aaa | ttt | ggt | tgg | aac | tta | ggt | aat | act | tta | gat | gct | caa | tgt | 2716 |
| Glu | Met | Lys | Phe | Gly | Trp | Asn | Leu | Gly | Asn | Thr | Leu | Asp | Ala | Gln | Cys | |
| | 45 | | | | | 50 | | | | | 55 | | | | | |

| | | | | | | | | | | | | | | | | |
|---|---|---|---|---|---|---|---|---|---|---|---|---|---|---|---|---|
| att | gat | aac | tta | gat | tat | gaa | aag | gat | caa | act | gct | tcc | gaa | act | tgc | 2764 |
| Ile | Asp | Asn | Leu | Asp | Tyr | Glu | Lys | Asp | Gln | Thr | Ala | Ser | Glu | Thr | Cys | |
| 60 | | | | | 65 | | | | | 70 | | | | | 75 | |

| | | | | | | | | | | | | | | | | |
|---|---|---|---|---|---|---|---|---|---|---|---|---|---|---|---|---|
| tgg | ggt | aat | cca | aaa | aca | acg | gag | gat | atg | ttc | aaa | gta | tta | atg | gat | 2812 |
| Trp | Gly | Asn | Pro | Lys | Thr | Thr | Glu | Asp | Met | Phe | Lys | Val | Leu | Met | Asp | |
| | | | 80 | | | | | 85 | | | | | 90 | | | |

| | | | | | | | | | | | | | | | | |
|---|---|---|---|---|---|---|---|---|---|---|---|---|---|---|---|---|
| aat | cag | ttc | aat | gtt | ttc | cgt | att | cca | act | act | tgg | tct | gga | cac | ttt | 2860 |
| Asn | Gln | Phe | Asn | Val | Phe | Arg | Ile | Pro | Thr | Thr | Trp | Ser | Gly | His | Phe | |
| | | | 95 | | | | | 100 | | | | | 105 | | | |

| | | | | | | | | | | | | | | | | |
|---|---|---|---|---|---|---|---|---|---|---|---|---|---|---|---|---|
| ggt | gaa | gca | cca | gat | tat | aag | att | aat | gaa | aaa | tgg | ttg | aaa | agg | gtt | 2908 |
| Gly | Glu | Ala | Pro | Asp | Tyr | Lys | Ile | Asn | Glu | Lys | Trp | Leu | Lys | Arg | Val | |
| | | 110 | | | | | 115 | | | | | 120 | | | | |

| | | | | | | | | | | | | | | | | |
|---|---|---|---|---|---|---|---|---|---|---|---|---|---|---|---|---|
| cat | gaa | gtt | gtt | gat | tat | gct | tac | aag | aat | gga | gcc | ttt | gta | atc | ttg | 2956 |
| His | Glu | Val | Val | Asp | Tyr | Ala | Tyr | Lys | Asn | Gly | Ala | Phe | Val | Ile | Leu | |
| | 125 | | | | | 130 | | | | | 135 | | | | | |

| | | | | | | | | | | | | | | | | |
|---|---|---|---|---|---|---|---|---|---|---|---|---|---|---|---|---|
| aat | att | cat | cac | gaa | act | tgg | aat | cat | gca | ttc | tcc | gaa | act | ctc | gaa | 3004 |
| Asn | Ile | His | His | Glu | Thr | Trp | Asn | His | Ala | Phe | Ser | Glu | Thr | Leu | Glu | |
| 140 | | | | | 145 | | | | | 150 | | | | | 155 | |

| | | | | | | | | | | | | | | | | |
|---|---|---|---|---|---|---|---|---|---|---|---|---|---|---|---|---|
| act | gct | aaa | gaa | att | ttg | gaa | aag | att | tgg | aca | caa | att | gca | gaa | gaa | 3052 |
| Thr | Ala | Lys | Glu | Ile | Leu | Glu | Lys | Ile | Trp | Thr | Gln | Ile | Ala | Glu | Glu | |
| | | | | 160 | | | | | 165 | | | | | 170 | | |

| | | | | | | | | | | | | | | | | |
|---|---|---|---|---|---|---|---|---|---|---|---|---|---|---|---|---|
| ttt | aag | gat | tat | gat | gaa | cat | tta | att | ttc | gaa | gga | tta | aat | gag | cca | 3100 |
| Phe | Lys | Asp | Tyr | Asp | Glu | His | Leu | Ile | Phe | Glu | Gly | Leu | Asn | Glu | Pro | |
| | | | 175 | | | | | 180 | | | | | 185 | | | |

| | | | | | | | | | | | | | | | | |
|---|---|---|---|---|---|---|---|---|---|---|---|---|---|---|---|---|
| aga | aag | aat | gat | aca | cca | gtt | gaa | tgg | aac | gga | ggt | gat | caa | gaa | gga | 3148 |
| Arg | Lys | Asn | Asp | Thr | Pro | Val | Glu | Trp | Asn | Gly | Gly | Asp | Gln | Glu | Gly | |
| | | 190 | | | | | 195 | | | | | 200 | | | | |

| | | | | | | | | | | | | | | | | |
|---|---|---|---|---|---|---|---|---|---|---|---|---|---|---|---|---|
| tgg | gat | gca | gtt | aat | gcc | atg | aat | gcg | gta | ttc | ctt | aag | aca | att | cgt | 3196 |
| Trp | Asp | Ala | Val | Asn | Ala | Met | Asn | Ala | Val | Phe | Leu | Lys | Thr | Ile | Arg | |
| | 205 | | | | | 210 | | | | | 215 | | | | | |

| | | | | | | | | | | | | | | | | |
|---|---|---|---|---|---|---|---|---|---|---|---|---|---|---|---|---|
| agt | tca | gga | ggt | aat | aat | tca | aaa | cgt | cat | ctt | atg | att | cca | cca | tat | 3244 |
| Ser | Ser | Gly | Gly | Asn | Asn | Ser | Lys | Arg | His | Leu | Met | Ile | Pro | Pro | Tyr | |
| 220 | | | | | 225 | | | | | 230 | | | | | 235 | |

| | | | | | | | | | | | | | | | | |
|---|---|---|---|---|---|---|---|---|---|---|---|---|---|---|---|---|
| gcg | gcc | gct | tgt | aat | gaa | aat | gcc | ttt | aag | aat | tac | att | ttc | cca | gaa | 3292 |
| Ala | Ala | Ala | Cys | Asn | Glu | Asn | Ala | Phe | Lys | Asn | Tyr | Ile | Phe | Pro | Glu | |
| | | | 240 | | | | | 245 | | | | | 250 | | | |

| | | | | | | | | | | | | | | | | |
|---|---|---|---|---|---|---|---|---|---|---|---|---|---|---|---|---|
| gat | gat | gat | aaa | gtt | att | gca | tca | gta | cat | gct | tat | caa | cca | tat | aac | 3340 |
| Asp | Asp | Asp | Lys | Val | Ile | Ala | Ser | Val | His | Ala | Tyr | Gln | Pro | Tyr | Asn | |
| | | | 255 | | | | | 260 | | | | | 265 | | | |

| | | | | | | | | | | | | | | | | |
|---|---|---|---|---|---|---|---|---|---|---|---|---|---|---|---|---|
| ttt | gcc | tta | aat | aat | gga | gaa | gga | gca | gtt | gat | aaa | ttt | gat | gca | aaa | 3388 |
| Phe | Ala | Leu | Asn | Asn | Gly | Glu | Gly | Ala | Val | Asp | Lys | Phe | Asp | Ala | Lys | |
| | | 270 | | | | | 275 | | | | | 280 | | | | |

| | | | | | | | | | | | | | | | | |
|---|---|---|---|---|---|---|---|---|---|---|---|---|---|---|---|---|
| tgc | aag | aat | gaa | ctt | ggt | tgg | aat | tta | gga | ata | atg | aag | aag | aga | ttt | 3436 |
| Cys | Lys | Asn | Glu | Leu | Gly | Trp | Asn | Leu | Gly | Ile | Met | Lys | Lys | Arg | Phe | |
| | 285 | | | | | 290 | | | | | 295 | | | | | |

| | | | | | | | | | | | | | | | | |
|---|---|---|---|---|---|---|---|---|---|---|---|---|---|---|---|---|
| gtt | gat | caa | ggt | att | cca | atg | att | ctt | gga | gaa | tat | ggt | gcc | atg | aat | 3484 |
| Val | Asp | Gln | Gly | Ile | Pro | Met | Ile | Leu | Gly | Glu | Tyr | Gly | Ala | Met | Asn | |
| 300 | | | | | 305 | | | | | 310 | | | | | 315 | |

| | | | | | | | | | | | | | | | | |
|---|---|---|---|---|---|---|---|---|---|---|---|---|---|---|---|---|
| cgt | gat | aat | gat | gaa | gaa | cgt | gct | aaa | tgg | gct | gaa | tat | tat | atg | gaa | 3532 |
| Arg | Asp | Asn | Asp | Glu | Glu | Arg | Ala | Lys | Trp | Ala | Glu | Tyr | Tyr | Met | Glu | |
| | | | | 320 | | | | | 325 | | | | | 330 | | |

```
aag gtt aca gca atg gga gtt cca caa gtc tgg tgg gat aat ggt att    3580
Lys Val Thr Ala Met Gly Val Pro Gln Val Trp Trp Asp Asn Gly Ile
            335                 340                 345 ttt gaa ggt gaa ggt gag cgt ttt gga ata ttt gat cgt tct aat ttg    3628
Phe Glu Gly Glu Gly Glu Arg Phe Gly Ile Phe Asp Arg Ser Asn Leu
350                 355                 360 aag att gtt tat cca ggc att gtt gca gcc tta caa aag gga aga gga    3676
Lys Ile Val Tyr Pro Gly Ile Val Ala Ala Leu Gln Lys Gly Arg Gly
    365                 370                 375 tta gaa gtt aat gtt gtt cat gcc gct gaa aca aag cca aag gaa gaa    3724
Leu Glu Val Asn Val Val His Ala Ala Glu Thr Lys Pro Lys Glu Glu
380                 385                 390                 395 aaa cca aag gaa taa ctcgagtcta gagggcccgt taaacccgc tgatcagcct     3779
Lys Pro Lys Glu cgactgtgcc ttctagttgc cagccatctg ttgtttgccc ctcccccgtg ccttccttga  3839
ccctggaagg tgccactccc actgtccttt cctaataaaa tgaggaaatt gcatcgcatt  3899
gtctgagtag gtgtcattct attctggggg gtggggtggg gcaggacagc aaggggagg   3959 attgggaaga caatagcagg catgctgggg a                                 3990

<210> SEQ ID NO 3
<211> LENGTH: 399
<212> TYPE: PRT
<213> ORGANISM: Artificial
<220> FEATURE:
<223> OTHER INFORMATION: Synthetic Construct

<400> SEQUENCE: 3

Ile Met Lys Pro Glu Pro Thr Glu Val Thr Thr Glu Ala Thr Thr Glu
1               5                   10                  15

Ala Thr Glu Ser Thr Glu Thr Thr Val Pro Ile Asn Pro Ser Thr Gly
                20                  25                  30

Ile Arg Asp Ile Ser Ser Lys Glu Leu Ile Lys Glu Met Lys Phe Gly
            35                  40                  45

Trp Asn Leu Gly Asn Thr Leu Asp Ala Gln Cys Ile Asp Asn Leu Asp
    50                  55                  60

Tyr Glu Lys Asp Gln Thr Ala Ser Glu Thr Cys Trp Gly Asn Pro Lys
65                  70                  75                  80

Thr Thr Glu Asp Met Phe Lys Val Leu Met Asp Asn Gln Phe Asn Val
                85                  90                  95

Phe Arg Ile Pro Thr Thr Trp Ser Gly His Phe Gly Ala Pro Asp
            100                 105                 110

Tyr Lys Ile Asn Glu Lys Trp Leu Lys Arg Val His Glu Val Val Asp
        115                 120                 125

Tyr Ala Tyr Lys Asn Gly Ala Phe Val Ile Leu Asn Ile His His Glu
    130                 135                 140

Thr Trp Asn His Ala Phe Ser Glu Thr Leu Glu Thr Ala Lys Glu Ile
145                 150                 155                 160

Leu Glu Lys Ile Trp Thr Gln Ile Ala Glu Glu Phe Lys Asp Tyr Asp
                165                 170                 175

Glu His Leu Ile Phe Glu Gly Leu Asn Glu Pro Arg Lys Asn Asp Thr
            180                 185                 190

Pro Val Glu Trp Asn Gly Gly Asp Gln Glu Gly Trp Asp Ala Val Asn
        195                 200                 205

Ala Met Asn Ala Val Phe Leu Lys Thr Ile Arg Ser Ser Gly Gly Asn
    210                 215                 220
```

```
Asn Ser Lys Arg His Leu Met Ile Pro Pro Tyr Ala Ala Ala Cys Asn
225                 230                 235                 240

Glu Asn Ala Phe Lys Asn Tyr Ile Phe Pro Glu Asp Asp Asp Lys Val
            245                 250                 255

Ile Ala Ser Val His Ala Tyr Gln Pro Tyr Asn Phe Ala Leu Asn Asn
        260                 265                 270

Gly Glu Gly Ala Val Asp Lys Phe Asp Ala Lys Cys Lys Asn Glu Leu
    275                 280                 285

Gly Trp Asn Leu Gly Ile Met Lys Lys Arg Phe Val Asp Gln Gly Ile
290                 295                 300

Pro Met Ile Leu Gly Glu Tyr Gly Ala Met Asn Arg Asp Asn Asp Glu
305                 310                 315                 320

Glu Arg Ala Lys Trp Ala Glu Tyr Tyr Met Glu Lys Val Thr Ala Met
                325                 330                 335

Gly Val Pro Gln Val Trp Trp Asp Asn Gly Ile Phe Glu Gly Glu Gly
            340                 345                 350

Glu Arg Phe Gly Ile Phe Asp Arg Ser Asn Leu Lys Ile Val Tyr Pro
        355                 360                 365

Gly Ile Val Ala Ala Leu Gln Lys Gly Arg Gly Leu Glu Val Asn Val
    370                 375                 380

Val His Ala Ala Glu Thr Lys Pro Lys Glu Glu Lys Pro Lys Glu
385                 390                 395

<210> SEQ ID NO 4
<211> LENGTH: 4023
<212> TYPE: DNA
<213> ORGANISM: Artificial
<220> FEATURE:
<221> NAME/KEY: CDS
<222> LOCATION: (2540)..(3772)
<223> OTHER INFORMATION: expression cassette

<400> SEQUENCE: 4
ctgacataag ctgaaccaat gccttgcata atacctgcaa tttagagtct ataagtaaaa      60
accacttatt gatcacatga gccatcgtgc tgttttttg ctaggaatat taactatgaa     120
atctgctctt aataaggttt atccagaatg acagtcatgt aaatccttat ttttttataac   180 attaatccaa tatcacttaa taacaacccg gaggttaaaa cctgccatac agaggagtac    240
ataactatgg ctgggaatat caatataagt ttcataaagg tattttttcca actgcatatg   300 aaagtaggag tagttactag ctattgaagg gtgatacaag aaagaagaaa agccctggaa    360
agtcatgaaa gaataaaatt gcttgtcaaa tacgcaaaat gtttattttt tgcgggagat    420
ggatattggg gactctgcac ttgtgttccg cccctctaac aatttgaaat attgaactcc    480
taactcccaa tggtatgcga ttaggctgtg ggtctttgg gaacaactta ggtcaaagtg    540
acatcatgag agtggaggcc ccatgatggg ttagtgtcct tgtacgaaga gaaagagaat   600
caggatctct gagctccaca ctccgtgagg atacaagaag cttgctgtct gtgaacatgg   660
aatgggcctt tcgcaagaca ctggagctgc tgatagtgta gtcttgggtt tcccagcctc   720
tagaaatgtg agaaagaaat atttgtgcta agccatccag cctatatggc attcttgtta   780
cagcagctgg aactgaatga gaaaaatagg acacggagta tgttcacgat gtgggctgga   840
ggagggaccg aaggagagtg ttgggattca cagagtgctc tcggaccccc tcacaaaagc    900
tagtacttcc tcactttttcc tcatcttagt aaatggtgtc atcagatacc tgtttcctca   960 attttttctct ttccccccagt cttcggtgct aatctatcga taaaccgatt gcttcgccac  1020
ctctgagata tattctatca gggccctaga gcagccactt tcctctttcg tggaccacta   1080
```

```
caaaagccta cctgatctct tggccccag tcgtgtcctc ctataatccg gttttcaca    1140
gcagagcaag aatggttttc ttggaaagga aatcagaatc tcttcactca tcttctttca   1200
gcctcaaaag ccctctcttt ccttatgttc tacaaggttc tacatgatct ggcctacctc   1260
tctgatttca tctcatttta ctcttccctt tgtcactcac acatgtttag ctgcactgat   1320
gttgaaagtt tgttcagtgt cacttgagta tcccacggtt gttcctacct tgggcttttg   1380
ctattgcact ttcctctatg gagactgctt ttcctctgat cttcaaataa gtgggtcctt   1440
ctactccttc cagttctggc tgacaatcac tccctctgaa acagctttcc tgactatttc   1500
cagtctaaaa tatcctgaaa aattcagtcc tttccccttt aactgcaccg tgggttcatg   1560
ctagttctca ctgctctctt taacttagta tcgttgttgt tatcattcca tcttgctata   1620
ttttccttac cttcccctag aatgtaggct gagaacaaga gtcttgtctg tcttgttcat   1680
ccttgtatcc tgagtatcat gccggcattt agcaaaagca ctcggccact acctgttgga   1740
tgaatggatt aggtttttcc cacctgtacg gttatgtctt tactaggatt tcttgtacct   1800
tacgaaggaa aatagatgtg gattcattaa cttagtgttt tagcacatat aagggacttt   1860
ttgctagaag gagaaaaaaa aaagtccatt ctttcctgct acagccagtg cattttcaca   1920
tgcgttaatg taagcgtggg gaaaaaaaaa tctgacacct aaagtcgtgg tcatttcact   1980
tccggataac ttcctaaatc ttagtggaga atctcaagta tctaacaact ggggtaggag   2040
gtaccaactg aactgagttg aataacatgt gtcttcttac aatggaaaca ttgcacgtgt   2100
ttacagacag ttagggcacc attgtgactg tgaattcagt tggctctaat tccgcctctg   2160
tcagtgaagg acttcagaaa taaaatctaa tcctacctaa acaatacatg attaagacct   2220
ttctgtagat aacatgccag atgtttcaaa acttgctgtt ccctcagtaa ggaaaacatt   2280
gtctgagaag gtcatttaga tagtattcct gggagatttt cgggatgttc ctcacctgtt   2340
tagtgtaatt atcaatagtt attttggag tatgcattca cggtttgtgc tctaagtatt   2400
tattcatgtc aatatttgct ttgtaaaata tgcttcttgc aggattataa atacttgccg   2460
ggaagaccgt tgacaacctc agagcaaaat gaagttgttt ctgctgcttt cagccattgg   2520
gttctgctgg gccggatcc cag agt gag ccg gag ctg aag ctg gaa agt gtg   2572
                     Gln Ser Glu Pro Glu Leu Lys Leu Glu Ser Val
                      1               5                      10 gtg att gtc agt cgt cat ggt gtg cgt gct cca acc aag gcc acg caa       2620
Val Ile Val Ser Arg His Gly Val Arg Ala Pro Thr Lys Ala Thr Gln
         15                  20                  25 ctg atg cag gat gtc acc cca gac gca tgg cca acc tgg ccg gta aaa       2668
Leu Met Gln Asp Val Thr Pro Asp Ala Trp Pro Thr Trp Pro Val Lys
             30                  35                  40 ctg ggt tgg ctg aca ccg cgc ggt ggt gag cta atc gcc tat ctc gga       2716
Leu Gly Trp Leu Thr Pro Arg Gly Gly Glu Leu Ile Ala Tyr Leu Gly
         45                  50                  55 cat tac caa cgc cag cgt ctg gta gcc gac gga ttg ctg gcg aaa aag       2764
His Tyr Gln Arg Gln Arg Leu Val Ala Asp Gly Leu Leu Ala Lys Lys
 60                  65                  70                  75 ggc tgc ccg cag tct ggt cag gtc gcg att att gct gat gtc gac gag       2812
Gly Cys Pro Gln Ser Gly Gln Val Ala Ile Ile Ala Asp Val Asp Glu
                 80                  85                  90 cgt acc cgt aaa aca ggc gaa gcc ttc gcc gcc ggg ctg gca cct gac       2860
Arg Thr Arg Lys Thr Gly Glu Ala Phe Ala Ala Gly Leu Ala Pro Asp
                     95                 100                 105 tgt gca ata acc gta cat acc cag aca gat acg tcc agt ccc gat ccg       2908
Cys Ala Ile Thr Val His Thr Gln Thr Asp Thr Ser Ser Pro Asp Pro
             110                 115                 120
```

```
tta ttt aat cct cta aaa act ggc gtt tgc caa ctg gat aac gcg aac      2956
Leu Phe Asn Pro Leu Lys Thr Gly Val Cys Gln Leu Asp Asn Ala Asn
125                 130                 135 gtg act gac gcg atc ctc agc agg gca gga ggg tta att gct gac ttt      3004
Val Thr Asp Ala Ile Leu Ser Arg Ala Gly Gly Leu Ile Ala Asp Phe
140                 145                 150                 155 acc ggg cat cgg caa acg gcg ttt cgc gaa ctg gaa cag gtg ctt aat      3052
Thr Gly His Arg Gln Thr Ala Phe Arg Glu Leu Glu Gln Val Leu Asn
                160                 165                 170 ttt ccg caa tca aac ttg tgc ctt aaa cgt gag aaa cag gac gaa agc      3100
Phe Pro Gln Ser Asn Leu Cys Leu Lys Arg Glu Lys Gln Asp Glu Ser
            175                 180                 185 tgt tca tta acg cag gca tta cca tcg gaa ctc aag gtg agc gcc gac      3148
Cys Ser Leu Thr Gln Ala Leu Pro Ser Glu Leu Lys Val Ser Ala Asp
        190                 195                 200 aat gtc tca tta acc ggt gcg gta agc ctc gca tca atg ctg acg gag      3196
Asn Val Ser Leu Thr Gly Ala Val Ser Leu Ala Ser Met Leu Thr Glu
    205                 210                 215 ata ttt ttc ttg caa caa gca cag gga atg ccg gag ccg ggg tgg gga      3244
Ile Phe Phe Leu Gln Gln Ala Gln Gly Met Pro Glu Pro Gly Trp Gly
220                 225                 230                 235 agg atc acc gat tca cac cag tgg aac acc ttg cta agt ttg cat aac      3292
Arg Ile Thr Asp Ser His Gln Trp Asn Thr Leu Leu Ser Leu His Asn
                240                 245                 250 gcg caa ttt tat ttg tta caa cgc acg cca gag gtt gcc cgc agc cgc      3340
Ala Gln Phe Tyr Leu Leu Gln Arg Thr Pro Glu Val Ala Arg Ser Arg
            255                 260                 265 gcc acc ccg tta tta gat ttg atc aag aca gcg ttg acg ccc cat cca      3388
Ala Thr Pro Leu Leu Asp Leu Ile Lys Thr Ala Leu Thr Pro His Pro
        270                 275                 280 ccg caa aaa cag gcg tat ggt gtg aca tta ccc act cca gtg ctg ttt      3436
Pro Gln Lys Gln Ala Tyr Gly Val Thr Leu Pro Thr Pro Val Leu Phe
    285                 290                 295 atc gcc gga cac gat act aat ctg gca aat ctc ggc ggc gca ctg gag      3484
Ile Ala Gly His Asp Thr Asn Leu Ala Asn Leu Gly Gly Ala Leu Glu
300                 305                 310                 315 ctc aac tgg acg ctt ccc ggt cag ccg gat aac acg ccg cca ggt ggt      3532
Leu Asn Trp Thr Leu Pro Gly Gln Pro Asp Asn Thr Pro Pro Gly Gly
                320                 325                 330 gaa ctg gtg ttt gaa cgc tgg cgt cgg cta agc gat aac agc cag tgg      3580
Glu Leu Val Phe Glu Arg Trp Arg Arg Leu Ser Asp Asn Ser Gln Trp
            335                 340                 345 att cag gtt tcg ctg gtc ttc cag act tta cag cag atg cgt gat aaa      3628
Ile Gln Val Ser Leu Val Phe Gln Thr Leu Gln Gln Met Arg Asp Lys
        350                 355                 360 acg ccg ctg tca tta aat acg ccg ccc gga gag gtg aaa ctg acc ctg      3676
Thr Pro Leu Ser Leu Asn Thr Pro Pro Gly Glu Val Lys Leu Thr Leu
    365                 370                 375 gca gga tgt gaa gag cga aat gcg cag ggc atg tgt tcg ttg gca ggt      3724
Ala Gly Cys Glu Glu Arg Asn Ala Gln Gly Met Cys Ser Leu Ala Gly
380                 385                 390                 395 ttt acg caa atc gtg aat gaa gca cgc ata ccg gcg tgc agt ttg taa      3772
Phe Thr Gln Ile Val Asn Glu Ala Arg Ile Pro Ala Cys Ser Leu
                400                 405                 410 ctcgagtcta gagggcccgt ttaaacccgc tgatcagcct cgactgtgcc ttctagttgc    3832
cagccatctg ttgtttgccc ctcccccgtg ccttccttga ccctggaagg tgccactccc    3892
actgtccttt cctaataaaa tgaggaaatt gcatcgcatt gtctgagtag gtgtcattct    3952
attctggggg gtgggtgggc aggacagc aaggggagg attgggaaga caatagcagg       4012
```
catgctgggg a                                                                                      4023

<210> SEQ ID NO 5
<211> LENGTH: 410
<212> TYPE: PRT
<213> ORGANISM: Artificial
<220> FEATURE:
<223> OTHER INFORMATION: Synthetic Construct

<400> SEQUENCE: 5

```
Gln Ser Glu Pro Glu Leu Lys Leu Glu Ser Val Val Ile Val Ser Arg
  1               5                  10                  15

His Gly Val Arg Ala Pro Thr Lys Ala Thr Gln Leu Met Gln Asp Val
             20                  25                  30

Thr Pro Asp Ala Trp Pro Thr Trp Pro Val Lys Leu Gly Trp Leu Thr
         35                  40                  45

Pro Arg Gly Gly Glu Leu Ile Ala Tyr Leu Gly His Tyr Gln Arg Gln
     50                  55                  60

Arg Leu Val Ala Asp Gly Leu Leu Ala Lys Lys Gly Cys Pro Gln Ser
 65                  70                  75                  80

Gly Gln Val Ala Ile Ile Ala Asp Val Asp Glu Arg Thr Arg Lys Thr
                 85                  90                  95

Gly Glu Ala Phe Ala Ala Gly Leu Ala Pro Asp Cys Ala Ile Thr Val
            100                 105                 110

His Thr Gln Thr Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Ser Arg Ala Gly Gly Leu Ile Ala Asp Phe Thr Gly His Arg Gln
145                 150                 155                 160

Thr Ala Phe Arg Glu Leu Glu Gln Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Phe Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Pro Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
```

```
                355                 360                 365
Asn Thr Pro Pro Gly Glu Val Lys Leu Thr Leu Ala Gly Cys Glu Glu
        370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410
```

```
<210> SEQ ID NO 6
<211> LENGTH: 22
<212> TYPE: DNA
<213> ORGANISM: Artificial
<220> FEATURE:
<223> OTHER INFORMATION: primer

<400> SEQUENCE: 6
gtaatacgac tcactatagg gc                                            22

<210> SEQ ID NO 7
<211> LENGTH: 19
<212> TYPE: DNA
<213> ORGANISM: Artificial
<220> FEATURE:
<223> OTHER INFORMATION: primer

<400> SEQUENCE: 7
actatagggc acgcgtggt                                                19

<210> SEQ ID NO 8
<211> LENGTH: 23
<212> TYPE: DNA
<213> ORGANISM: Artificial
<220> FEATURE:
<223> OTHER INFORMATION: primer

<400> SEQUENCE: 8
gctgaaagca gcagaaactt cat                                           23

<210> SEQ ID NO 9
<211> LENGTH: 26
<212> TYPE: DNA
<213> ORGANISM: Artificial
<220> FEATURE:
<223> OTHER INFORMATION: primer

<400> SEQUENCE: 9
atgaacaata gacgttcgtc cagact                                        26

<210> SEQ ID NO 10
<211> LENGTH: 27
<212> TYPE: DNA
<213> ORGANISM: Artificial
<220> FEATURE:
<223> OTHER INFORMATION: primer

<400> SEQUENCE: 10
taccgctcac attcaagagc aatgtca                                       27

<210> SEQ ID NO 11
<211> LENGTH: 23
<212> TYPE: DNA
<213> ORGANISM: Artificial
<220> FEATURE:
<223> OTHER INFORMATION: primer

<400> SEQUENCE: 11
```

```
gcggccgcct gacataagct gaa                                              23

<210> SEQ ID NO 12
<211> LENGTH: 23
<212> TYPE: DNA
<213> ORGANISM: Artificial
<220> FEATURE:
<223> OTHER INFORMATION: primer

<400> SEQUENCE: 12
gatatcggcc cagcagaacc caa                                              23

<210> SEQ ID NO 13
<211> LENGTH: 25
<212> TYPE: DNA
<213> ORGANISM: Artificial
<220> FEATURE:
<223> OTHER INFORMATION: primer

<400> SEQUENCE: 13
gctagcctga cataagctga accaa                                            25

<210> SEQ ID NO 14
<211> LENGTH: 23
<212> TYPE: DNA
<213> ORGANISM: Artificial
<220> FEATURE:
<223> OTHER INFORMATION: primer

<400> SEQUENCE: 14
ggatccggcc cagcagaacc caa                                              23

<210> SEQ ID NO 15
<211> LENGTH: 24
<212> TYPE: DNA
<213> ORGANISM: Artificial
<220> FEATURE:
<223> OTHER INFORMATION: primer

<400> SEQUENCE: 15
ggatccatta tgaaacccga acca                                             24

<210> SEQ ID NO 16
<211> LENGTH: 24
<212> TYPE: DNA
<213> ORGANISM: Artificial
<220> FEATURE:
<223> OTHER INFORMATION: primer

<400> SEQUENCE: 16
ctcgagttat tcctttggtt tttc                                             24

<210> SEQ ID NO 17
<211> LENGTH: 23
<212> TYPE: DNA
<213> ORGANISM: Artificial
<220> FEATURE:
<223> OTHER INFORMATION: primer

<400> SEQUENCE: 17
ggatcccaga gtgagccgga gct                                              23

<210> SEQ ID NO 18
<211> LENGTH: 26
<212> TYPE: DNA
<213> ORGANISM: Artificial
```

```
<220> FEATURE:
<223> OTHER INFORMATION: primer

<400> SEQUENCE: 18
ctcgagttac aaactgcacg ccggta                                              26

<210> SEQ ID NO 19
<211> LENGTH: 20
<212> TYPE: DNA
<213> ORGANISM: Artificial
<220> FEATURE:
<223> OTHER INFORMATION: primer

<400> SEQUENCE: 19
agggaccgaa ggagagtgtt                                                     20

<210> SEQ ID NO 20
<211> LENGTH: 21
<212> TYPE: DNA
<213> ORGANISM: Artificial
<220> FEATURE:
<223> OTHER INFORMATION: primer

<400> SEQUENCE: 20
accattcttg ctctgctgtg a                                                   21

<210> SEQ ID NO 21
<211> LENGTH: 21
<212> TYPE: DNA
<213> ORGANISM: Artificial
<220> FEATURE:
<223> OTHER INFORMATION: primer

<400> SEQUENCE: 21
accgttgaca acctcagagc a                                                   21

<210> SEQ ID NO 22
<211> LENGTH: 21
<212> TYPE: DNA
<213> ORGANISM: Artificial
<220> FEATURE:
<223> OTHER INFORMATION: primer

<400> SEQUENCE: 22
tcgttcacca aagtgtccag a                                                   21

<210> SEQ ID NO 23
<211> LENGTH: 19
<212> TYPE: DNA
<213> ORGANISM: Artificial
<220> FEATURE:
<223> OTHER INFORMATION: primer

<400> SEQUENCE: 23
cattgttgca gccttacaa                                                      19

<210> SEQ ID NO 24
<211> LENGTH: 19
<212> TYPE: DNA
<213> ORGANISM: Artificial
<220> FEATURE:
<223> OTHER INFORMATION: primer

<400> SEQUENCE: 24
actcagacaa tgcgatgca                                                      19
```

-continued

```
<210> SEQ ID NO 25
<211> LENGTH: 22
<212> TYPE: DNA
<213> ORGANISM: Artificial
<220> FEATURE:
<223> OTHER INFORMATION: primer

<400> SEQUENCE: 25
accgttgaca acctcagagc aa                                              22

<210> SEQ ID NO 26
<211> LENGTH: 22
<212> TYPE: DNA
<213> ORGANISM: Artificial
<220> FEATURE:
<223> OTHER INFORMATION: primer

<400> SEQUENCE: 26
acgctcgtcg acatcagcaa ta                                              22

<210> SEQ ID NO 27
<211> LENGTH: 18
<212> TYPE: DNA
<213> ORGANISM: Artificial
<220> FEATURE:
<223> OTHER INFORMATION: primer

<400> SEQUENCE: 27
tcggctaagc gataacag                                                   18

<210> SEQ ID NO 28
<211> LENGTH: 20
<212> TYPE: DNA
<213> ORGANISM: Artificial
<220> FEATURE:
<223> OTHER INFORMATION: primer

<400> SEQUENCE: 28
acaacagatg gctggcaact                                                 20

<210> SEQ ID NO 29
<211> LENGTH: 24
<212> TYPE: DNA
<213> ORGANISM: Artificial
<220> FEATURE:
<223> OTHER INFORMATION: primer

<400> SEQUENCE: 29
ggatccttat tcctttggtt tttc                                            24

<210> SEQ ID NO 30
<211> LENGTH: 24
<212> TYPE: DNA
<213> ORGANISM: Artificial
<220> FEATURE:
<223> OTHER INFORMATION: primer

<400> SEQUENCE: 30
ggatccttac aaactgcacg ccgg                                            24

<210> SEQ ID NO 31
<211> LENGTH: 20
<212> TYPE: DNA
<213> ORGANISM: Artificial
<220> FEATURE:
<223> OTHER INFORMATION: primer

<400> SEQUENCE: 31
```

```
tccgttccat tcaactggtg                                            20

<210> SEQ ID NO 32
<211> LENGTH: 21
<212> TYPE: DNA
<213> ORGANISM: Artificial
<220> FEATURE:
<223> OTHER INFORMATION: primer

<400> SEQUENCE: 32
tcagtcacgt tcgcgttatc t                                          21
```

PORCINE PANCREATIC AMYLASE GENE PROMOTER AND TRANSGENIC PIGS EXPRESSING HETEROLOGOUS DIGESTIVE ENZYMES

FIELD OF THE INVENTION

The present invention relates generally to the expression of heterologous proteins in animals and to the production of transgenic animals.

BACKGROUND OF THE INVENTION

Animal husbandry constitutes the biggest portion of agricultural production in Taiwan, and brings handsome and stable income to Taiwanese farmers. However, fecal waste produced by livestock in large amount is not properly disposed and thus results in environmental pollution. According to the statistical information from the Council of Agriculture, Executive Yuan, Taiwan, the headcount of farmed hogs was 6,794,000 by the end of the year 2002. Assuming that each hog produces 6 Kg of fecal waste per day, there will be about 15,000,000 metric tons of hog fecal waste per year, plus the fecal waste from poultry. The serious environmental pollution resulting from such a large amount of fecal waste has become the major problem in Taiwanese animal husbandry. How to reduce the production of fecal waste without jeopardizing farmers' income is an important issue.

In addition to the aforementioned environmental issue, Taiwanese animal husbandry has to compete with imported livestock products since Taiwan joined the World Trade Organization (WTO) in 2002. How to reduce the production cost while enhancing the production rate has become another important issue. Generally speaking, the cost of feed constitutes 60 to 70% of the total production cost. Therefore, the key to reduce the production cost is to improve feed utilization. Effective ways include utilizing biotechnology to develop feed additives for enhancing the digestion of feed, and breeding livestock animals able to digest cellulose to reduce fecal production.

The quantity and quality of animal feces depend on the digestion and utilization of the components of feed by the animal. Generally speaking, livestock animals do not have the ability to synthesize digestive enzymes such as cellulases and phytases, and thus cannot effectively digest the cellulose and plant phosphorus in the feed. Such inability affects feed utilization and results in a waste of feed. In addition, the undigested nutrients are excreted from the animals and become a cause of environmental pollution. A common method for enhancing utilization of the nutrients in feed by animals is to supplement the feed with certain digestive enzymes produced on large scale by microorganisms. Recently, the cDNAs of several digestive enzymes have been screened out from fungal and bacterial cDNA libraries, and the enzymes have been produced on large scale by E. coli (Ye et al., 2001, Inter. J. Biochem. Biol. 33:87-94; and Zhang et al., 1998, Biotechnol. Lett. 20: 1001-1005; both hereby incorporated herein by reference). However, the production cost of this method is high. In addition, the supplementary digestive enzymes are usually destroyed in the animal's digestive tract by the native enzymes or gastric acid and thus cannot carry out their function.

Since the 1980s, the generation of transgenic animals not only allows us to study gene functions in vivo, but also provides a new way to improve the genetics of livestock animals. In the conventional breeding method, it takes tens of or even over a hundred years to improve the genetics of livestock animals. However, utilizing the techniques of genetic transformation, the same improvement can be achieved within one generation. In 1985, Hammer et al. first published their results in transgenic pigs, sheep and rabbits (Hammer et al., 1985, Nature 315:680-683; hereby incorporated herein by reference). Afterwards, researchers have utilized genes encoding growth factors from various animals (including cattle, mice and humans) to generate transgenic pigs carrying heterologous growth factor genes, hoping to increase lean meat in pigs and to shorten rearing time (Pursel and Rexroad, 1993, J. Anim. Sci. 71:10-19; hereby incorporated herein by reference). For example, Pursel et al. have constructed several heterologous growth factor genes under the control of the mouse metallothionein-I promoter (Pursel et al., 1989, Science 244:1281-1288; hereby incorporated herein by reference), and thereby the transcription of the heterologous genes can be induced and regulated effectively by the addition of trace amounts of zinc in the feed.

As known in the art, manipulation of animals (such as pigs) to alter and/or improve phenotypic characteristics (such as productivity or quality) requires the expression of heterologous genes in animal tissues. Such genetic manipulation therefore relies on the availability of means to drive and to control gene expression as required; for example, on the availability and use of suitable promoters which are effective in animals and which regulate gene expression so as to give the desired effect(s) in the transgenic animal. It is advantageous to have the choice of a variety of different promoters so that the most suitable promoter may be selected for a particular gene, construct, cell, tissue, animal or environment.

There is a continuing need in the art for high-level expression promoters, as well as promoters which are spatially defined in their expression patterns.

BRIEF SUMMARY OF THE INVENTION

In the present invention, a novel porcine pancreatic amylase gene promoter is operatively linked to either a fungal cellulase gene or a bacterial phytase gene to form an expression cassette, which is utilized in the generation of transgenic mice and pigs.

Accordingly, in one aspect, the present invention provides an isolated porcine pancreatic amylase gene promoter. In a preferred embodiment, the promoter has a nucleotide sequence as set forth in SEQ ID NO: 1.

In another aspect, the present invention provides a recombinant DNA construct comprising the porcine pancreatic amylase gene promoter of the present invention operatively linked to a nucleotide sequence of interest. In a preferred embodiment, the nucleotide sequence of interest codes for a digestive enzyme, such as a phytase, a cellulase, a glucanase and a xylanase.

In a further aspect, the present invention provides a method for producing a transgenic animal comprising the steps of providing an animal embryo and introducing into the animal embryo a transgene comprising the porcine pancreatic amylase gene promoter of the present invention operatively linked to a nucleotide sequence of interest, thereby transforming the embryo with the transgene.

In yet another aspect, the present invention provides a transgenic animal whose genome contains a transgene comprising a heterologous nucleotide sequence operatively linked to the promoter of the present invention. In a preferred embodiment, the transgenic animal is a pig.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
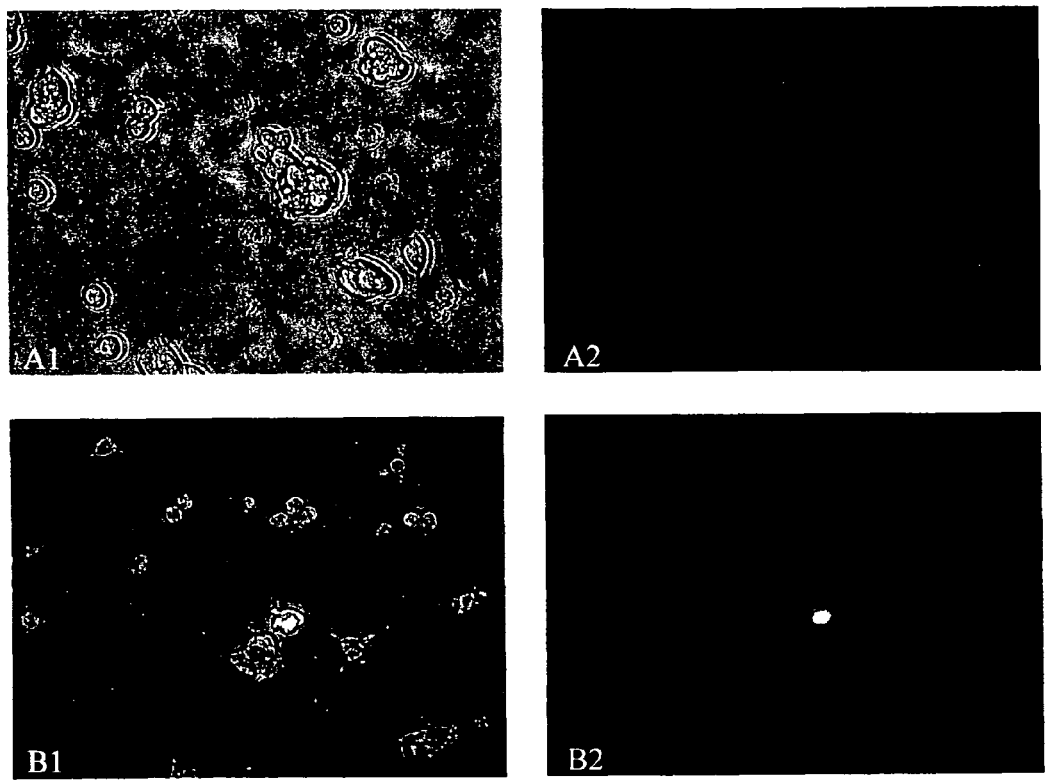
FIG. 1 shows fluorescence microscopic images of AR-42J rat pancreatic tumor cells transfected with 412 pAMY-phrGFP or 1216 pAMY-phrGFP vectors. Panel A1 is the image of 1216 pAMY-phrGFP-transfected AR-42J cells under bright field. Panel A2 is the image of 1216 pAMY-phrGFP-transfected AR-42J cells under dark field. Panel B1 is the image of 412 pAMY-phrGFP-transfected AR-42J cells under bright field. Panel B2 is the image of 412 pAMY-phrGFP-transfected AR-42J cells under dark field.

As noted above, the present invention is directed to a novel promoter sequence of the porcine pancreatic amylase gene and uses thereof in the expression of recombinant genes and production of transgenic animals. The promoter of the present invention permits space and time-determined expression of transgenes in a transgenic animal.

In accordance with an embodiment of the present invention, there is provided an isolated porcine pancreatic amylase gene promoter.

As used herein, the term "isolated" refers to material, such as a nucleic acid, which is substantially or essentially free from components that normally accompany or interact with it as found in its naturally occurring environment. The isolated material optionally comprises material not found with the material in its natural environment.

As used herein, the term "promoter" refers to an untranslated DNA sequence upstream of a coding region that contains the binding site for an RNA polymerase and initiates transcription of the coding region. The promoter region may also include other elements that act as regulators of gene expression.

In a preferred embodiment, the promoter of the present invention has the nucleotide sequence of SEQ ID NO: 1.

In accordance with another embodiment of the present invention, there is provided a recombinant DNA construct comprising the porcine pancreatic amylase gene promoter of the present invention operatively linked to a nucleotide sequence of interest.

In a preferred embodiment, the recombinant DNA construct is an expression vector comprising an expression cassette. As used herein, the term "expression cassette" refers to a nucleic acid construct, generated recombinantly or synthetically, with a series of specified nucleic acid elements which permit transcription of a nucleotide sequence of interest in a host cell. The expression cassette can be incorporated into a plasmid, chromosome, mitochondrial DNA, plastid DNA, virus, or nucleic acid fragment. Typically, the expression cassette portion of an expression vector includes, among other sequences, a nucleotide sequence to be transcribed, and a promoter. In the present invention, the expression cassette can also be referred to as a "transgene" when used to produce transgenic animals.

As used herein, "operatively linked" includes reference to a functional linkage between a promoter and a second sequence, wherein the promoter sequence initiates and mediates transcription of the second sequence. Generally, "operatively linked" means that the nucleic acid sequences being linked are contiguous and, where necessary to join two protein coding regions, contiguous and in the same reading frame.

According to the present invention, the nucleotide sequence of interest under the control of the promoter can be any nucleic acid form. Correspondingly they can be coding nucleic acids or structural or functional nucleic acids. The term "coding nucleic acid" is understood to mean more particularly a nucleic acid coding for a peptide or protein. The peptide or protein can e.g. be a structural protein or a peptide or protein having enzymatic activity. A "structural nucleic acid" is more particularly understood to mean a nucleic acid leading to the formation of complexes, particularly with other molecules. It can inter alia be an rRNA and in particular an antisense nucleic acid. A "functional nucleic acid" is more particularly understood to mean a nucleic acid, which exerts a specific action on a system, particularly a biological system. Such a specific action can e.g. be the aiding or inhibiting of translation or transcription. An example of a functional nucleic acid is an antisense nucleic acid.

As used herein, the singular forms "a", "an", and "the" include plural referents unless the context clearly indicates otherwise.

In a preferred embodiment, the nucleotide sequence of interest under the control of the promoter is a coding nucleic acid. More preferably, the coding nucleic acid codes for a digestive enzyme, such as a phytase, a cellulase, a glucanase or a xylanase.

In accordance with a further embodiment of the present invention, there is provided a method for producing a transgenic animal comprising the steps of providing an animal embryo and introducing into the animal embryo a transgene comprising the porcine pancreatic amylase gene promoter of the present invention operatively linked to a nucleotide sequence of interest, thereby transforming the embryo with the transgene.

According to the present invention, the transgenic animal is preferably a mammal, more preferably livestock such as cattle, sheep or pigs. In a preferred embodiment, the transgenic animal of the present invention is a pig.

Generation of transgenic animals of the present invention is carried out conventionally by techniques well known in the art. There are a number of techniques that permit the introduction of genetic material (such as a transgene) into animals to be transformed, including the viral infection technique; the sperm mediated gene transfer (SMGT) technique; the embryonic stem cell technique; the nuclear transfer technique; and the pronuclear microinjection technique. Among them, the most commonly used technique is the pronuclear microinjection technique, which comprises direct injection of the transgene into the male pronucleus of fertilized eggs, resulting in the random integration into one locus of a varying number of copies, usually in a head to tail array. The injected eggs are then re-transferred into the uteri of pseudo-pregnant recipient mothers. Some of the resulting offspring may have one or several copies of the transgene integrated into their genomes, usually in one integration site. An advantage of the pronuclear microinjection technique is that the transgene would be stably integrated into the germline of transgenic animals so that it will be passed to their offspring.

According to a preferred embodiment of the present invention, the transgene is introduced into the embryo by pronuclear microinjection.

Preferably, prior to the introduction of the transgene into the embryo, it is removed from the vector portion by restriction enzyme digestion, for example by using restriction sites in the vector that flank the transgene. For cloning purposes, the transgene is generally inserted into an expression vector, such as the mammalian expression vector pCR® 3.1 (Invitrogen Corporation), prior to the introduction into the embryo. In general, the transgenic DNA sequence is inserted into an appropriate restriction endonuclease site(s) by procedures known in the art. Such procedures and others are deemed to be within the scope of those skilled in the art.

In accordance with yet another embodiment of the present invention, there is provided a transgenic animal whose genome contains a transgene comprising a heterologous nucleotide sequence operatively linked to the promoter of the present invention. In a preferred embodiment, the transgenic animal is a pig.

As used herein, the term "heterologous" in reference to a nucleic acid is a nucleic acid that originates from a foreign species, or, if from the same species, is substantially engineered from its native form in composition and/or genomic locus by deliberate human intervention. A heterologous protein may originate from a foreign species or, if from the same species, is substantially engineered from its original form by deliberate human intervention.

Preferably, the transgenic animal is generated by introduction of a transgene into an embryo by pronuclear microinjection, insertion of the embryo into a surrogate mother, and allowing the embryo to develop to term.

The present invention is further illustrated by the following examples, which are provided for the purpose of demonstration rather than limitation.

Example 1 Cloning of Porcine Pancreatic Amylase Gene Promoter

Darnis et al. has obtained the nearly full-length cDNA sequence of porcine pancreatic a-amylase gene (GenBank Accession No. AF064742) from a cDNA library constructed with the mRNA isolated from pancreatic tissues of pigs (Darnis et al., 1999, Biochem Biophys Acta. 1430:281-289; hereby incorporated herein by reference). The cDNA sequence has a length of 1,536 bp, and encodes a protein of 496 amino acids with a signal peptide of 15 amino acids. Based on the cDNA sequence, the promoter was cloned utilizing GenomeWalker™ Kit (Clontech Laboratories, Inc., Mountain View, Calif., USA) according to the manufacturer's instructions.

First, the genomic DNA isolated from porcine blood was digested at 37° C. by the four restriction enzymes (Dra I, EcoR V, Pvu II, and Stu I) provided in the kit. After 16 hours, the digested genomic DNA was precipitated by ethanol and resuspended. The resuspended digested genomic DNA was then ligated to the adaptor provided in the kit at 16° C. for 16 hours.

In addition to the two "adaptor primers" (AP1 and AP2) provided in the kit, three primers, GSP1, GSP2 and GSP3 were designed based on the sequence at the 5' end of the porcine pancreatic amylase gene (see Table 1). The first PCR was conducted utilizing the above-derived digested genomic DNA as a template and GSP3 and AP1 as primers. The second PCR was conducted utilizing the products of the first PCR as a template and GSP2 and AP2 as primers. The products of the second PCR were screened by gel electrophoresis, and possible fragments (i.e., those larger than 1 kb) were recovered from the gel and purified.

The selected fragments were cloned into pGEM®-T Easy Vectors (Promega Corporation, Madison, Wis., USA) and the formed vectors were named pGEM-T AMY. The clones were sequenced and two clones, numbered 412 and 1216, were selected.

TABLE 1

Primers Used in Genome Walking

| Primer | Sequence | Tm value (° C.) |
|---|---|---|
| AP1 | GTAATACGACTCACTATAGGGC (SEQ ID NO: 6) | 59 |
| AP2 | ACTATAGGGCACGCGTGGT (SEQ ID NO: 7) | 71 |
| GSP1 | GCTGAAAGCAGCAGAAACTTCAT (SEQ ID NO: 8) | 60.4 |
| GSP2 | ATGAACAATAGACGTTCGTCCAGACT (SEQ ID NO: 9) | 59.7 |
| GSP3 | TACCGCTCACATTCAAGAGCAATGTCA (SEQ ID NO: 10) | 62.3 |

Example 2 Activity Test of Porcine Pancreatic Amylase Gene Promoter

To test the activity of the promoter cloned in Example 1, new primers (1216AMY-GFP-NotI-5' and 1216AMY-GFP- EcoRV-3') (see Table 2) were designed in order to create an Not I restriction site at the 5' end and an EcoR V restriction site at the 3' end of the promoter by PCR. The PCR products were again cloned into pGEM®-T Easy Vectors and digested with the relevant restriction enzymes. The digested fragments were cloned into phrGFP vectors (Stratagene, La Jolla, Calif., USA) and the clones were sequenced. Two clones, 412 pAMY-phrGFP and 1216 pAMY-phrGFP, were obtained.

Rat pancreatic tumor cell line AR-42J (BCRC 60160) was purchased from the Bioresource Collection and Research Center of Food Industry Research and Development Institute, Hsinchu, Taiwan. The cells were cultured on a six-well culture plate, with each well containing $7 \times 10^4$ cells. The cultured cells were transfected with lipofectomine (Invitrogen Corporation, Carlsbad, Calif., USA) and either 412 pAMY-phrGFP or 1216 pAMY-phrGFP vectors. After culturing at 37° C. for 24 hours, green fluorescence was observed using a fluorescent microscope (FIG. 1). These results showed that the cloned promoter was able to drive the expression of heterologous genes (in this case, the coding sequence for green fluorescence protein) in pancreatic cells.

TABLE 2

Primers Used in Constructing 1216pAMY-phrGFP, 1216pAMY-CEL and pAMY-PHY

| Primer | Sequence | Tm value (° C.) |
|---|---|---|
| 1216AMY-GFP-NotI-5' | GCGGCCGCCTGACATAAGCTGAA (SEQ ID NO: 11) | 79.5 |
| 1216AMY-GFP-EcoRV-3' | GATATCGGCCCAGCAGAACCCAA (SEQ ID NO: 12) | 76.4 |
| 1216AMY-NheI-5' | GCTAGCCTGACATAAGCTGAACCAA (SEQ ID NO: 13) | 71.8 |
| 1216AMY-BamHI-3' | GGATCCGGCCCAGCAGAACCCAA (SEQ ID NO: 14) | 82.0 |
| CEL-BamHI-5' | GGATCCATTATGAAACCCGAACCA (SEQ ID NO: 15) | 69.7 |
| CEL-XhoI-3' | CTCGAGTTATTCCTTTGGTTTTTC (SEQ ID NO: 16) | 66.6 |
| PHY-BamHI-5' | GGATCCCAGAGTGAGCCGGAGCT (SEQ ID NO: 17) | 74.1 |
| PHY-XhoI-3' | CTCGAGTTACAAACTGCACGCCGGTA (SEQ ID NO: 18) | 78.1 |

Example 3 Preparation of Transgene Constructs for Microinjection

A cellulase gene (GenBank Accession No. AF053363) from *Piromyces rhizinflatus* and a phytase gene (GenBank Accession No. AF537219) from an *E. coli* strain isolated from bovine feces (ATCC 33965) were used to construct the transgenes. cDNAs of both genes were provided by Dr. Kuo-Joan Cheng of Institute of Bioagricultural Science, Academia Sinica, Taipei, Taiwan. The cDNAs of both genes were first amplified by PCR using primer pairs CEL-BamHI-5'+CEL-XhoI-3' (for the cellulase gene) and PHY-BamHI5'+PHY-XhoI-3' (for the phytase gene) (see Table 2) and cloned into pGEM®-T Easy Vectors. The promoter cloned in Example 1 was also amplified by PCR using primer pair 1216AMY-NheI-5'+1216AMY-BamHI-3' (see Table 2) and the PCR products were also cloned into pGEM®-T Easy Vectors.

The promoter (digested with Nhe I and BamH I) and either the cellulase or phytage gene (digested with BamH I and Xho I) were cloned into the mammalian expression vector pCR® 3.1 (Invitrogene Corporation) to form the vector pAMY-CEL or pAMY-PHY. After mass production of the vectors, a transgene (SEQ ID NO:2) containing the promoter, a signal peptide, a structural gene expressing a polypeptide having the sequence of SEQ ID NO:3 and a BGH poly A tail and a transgene (SEQ ID NO:4) containing the promoter, the signal peptide, a structural gene expressing a polypeptide having the sequence of SEQ ID NO:5, and a BGH poly A tail were excised from the vectors by restriction enzyme digestion. The excised transgenes were recovered trice with QIAquick Gel Extraction Kit (Qiagen Inc., Valencia, Calif., USA) and subjected to CsCl density gradient centrifugation (CsCl, 1 gm/ml; ethylene bromide (EthBr), 24 µl; DNA, 100-200 µg, 0.02% Triton-X100) at 100,000 rpm for 6 hrs. After centrifugation, the band containing linear DNA was extracted under UV light and mixed with saturated butanol aqueous solution to remove EtBr. The DNA was then dialyzed with TE buffer (pH 8.0) for 24 hours to remove CsCl, precipitated with ethanol, and redissolved in TE buffer (pH 7.4). After the concentration and quality of the DNA were determined by gel electrophoresis and a spectrophotometer, the DNA was diluted to 3 ng/µl and stored under −20° C.

Example 4 Production of Transgenic Mice

The ICR female mice used as embryo donors and recipients were purchased from National Taiwan University Animal Center (Taipei, Taiwan). The present experiment was conducted on 6 to 7 week old, sexually mature female mice.

Fertilized mouse embryos of the pronucleus stage were flushed out and recovered from the oviducts of superovulated female mice. Ten to twenty embryos to be microinjected were placed into a microdrop of M2 buffer in the center of a depression microscope slide. The microdrop was covered with heavy mineral oil to prevent evaporation of the buffer. Microinjection was performed using a differential interference contrast microscope (Axiovert 10, Zeiss, Germany) with Narashigi NT-8 micromanipulators (Narashigi, Japan). The holding pipette for stabilizing the embryo and the injection pipette for DNA injection were prepared as described in Wu et al., 1995, J. Chin. Soc. Anim. Sci. 24:181-189 (hereby incorporated herein by reference). About 2 pl of DNA solution containing 3 to 5 ng/µl of the transgene constructs prepared in Example 3 were injected into the male pronucleus of each embryo.

Embryos surviving the microinjection process as judged by morphological observation (i.e., those retaining dense deutoplasm and intact appearance) were implanted into recipient females made pseudo-pregnant by mating with vasectomized males. About 10 to 20 microinjected mouse embryos were transferred into each of the two oviducts of pseudopregnant females. Embryos were allowed to come to term and the newborn mice were analyzed for the presence of the transgenes by PCR as described below.

In the present study, 267 ICR mouse embryos were microinjected with the transgenes, among which 245 surviving embryos were implanted into the oviducts of recipient female mice (the loss rate for microinjected embryos was 8.2%). A total of 63 mouse pups were born, meaning that the survival rate for mouse embryos was 25.7%.

Example 5 Analysis of Transgenic Mouse Genomic DNA

Among the 63 potential transgenic mouse pups obtained in Example 4, only 57 have successfully grown up to weaning age. Using tissue samples removed from the tails of the 57 surviving pups, genomic DNA was obtained by the following procedures.

The tissue sample was cut into tiny pieces and mixed with a solution containing 630 μl of tissue lysis buffer (100 mM Tris-HCl (pH 8.5), 5 mM EDTA, 200 mM NaCl), 70 μl of 10% SDS, and 35 μl of 100 mg/ml Proteinase K. The mixture was incubated in a 55° C. water bath for 12 to 16 hours, and then centrifuged at 12,000× rpm for 5 minutes. The supernatant from centrifugation was extracted twice with phenol/chloroform (1:1), and then centrifuged at 12,000× rpm again for 5 minutes to obtain two layers. DNA was precipitated from the upper layer with absolute ethanol, washed with 70% ethanol, and redissolved in autoclaved distilled and deionized H$_2$O.

PCR reactions on the genomic DNA samples obtained above were carried out conventionally. Primer pairs were designed based on the sequences of the porcine pancreatic amylase gene promoter, the junction between the promoter and the structural gene, the structural gene, and the BGH poly A tail (Table 3). To primarily examine if a potential transgenic mouse carries the desired transgene, the genomic DNA sample was subjected to PCR (reaction volume=20 μl) using either primer pair 1216-pF+CEL-R (for the cellulase gene) or 1216-pF+PHY-R (for the phytase gene). For the cellulase gene, the reaction conditions were: (1) 94° C., 2 mins; (2) 94° C., 30 secs; 65° C., 30 secs; and 72° C., 2 mins; 35 cycles; (3) 72° C., 7 mins; and (4) 4° C., termination. For the phytase gene, the reaction conditions were: (1) 94° C., 2 mins; (2) 94° C., 30 secs; 67° C., 30 secs; and 72° C., 2 mins; 35 cycles; (3) 72° C., 7 mins; and (4) 4° C., termination.

Figure 2:
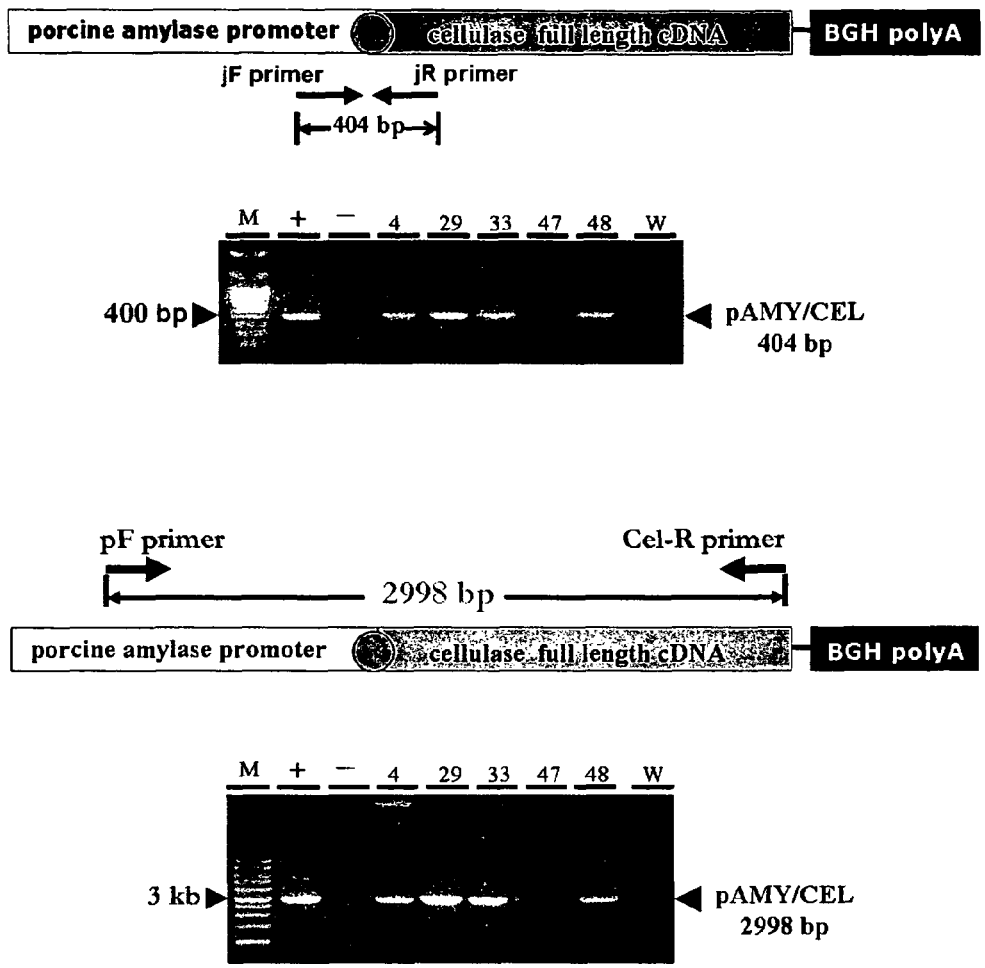
FIG. 2 shows the results of PCR verification of transgenic mice harboring the cellulase transgene. "M" denotes markers; "+" denotes positive control; "−" denotes negative control; and "W" denotes wildtype. The numbers correspond to the identification numbers of the transgenic mice.
Figure 3:
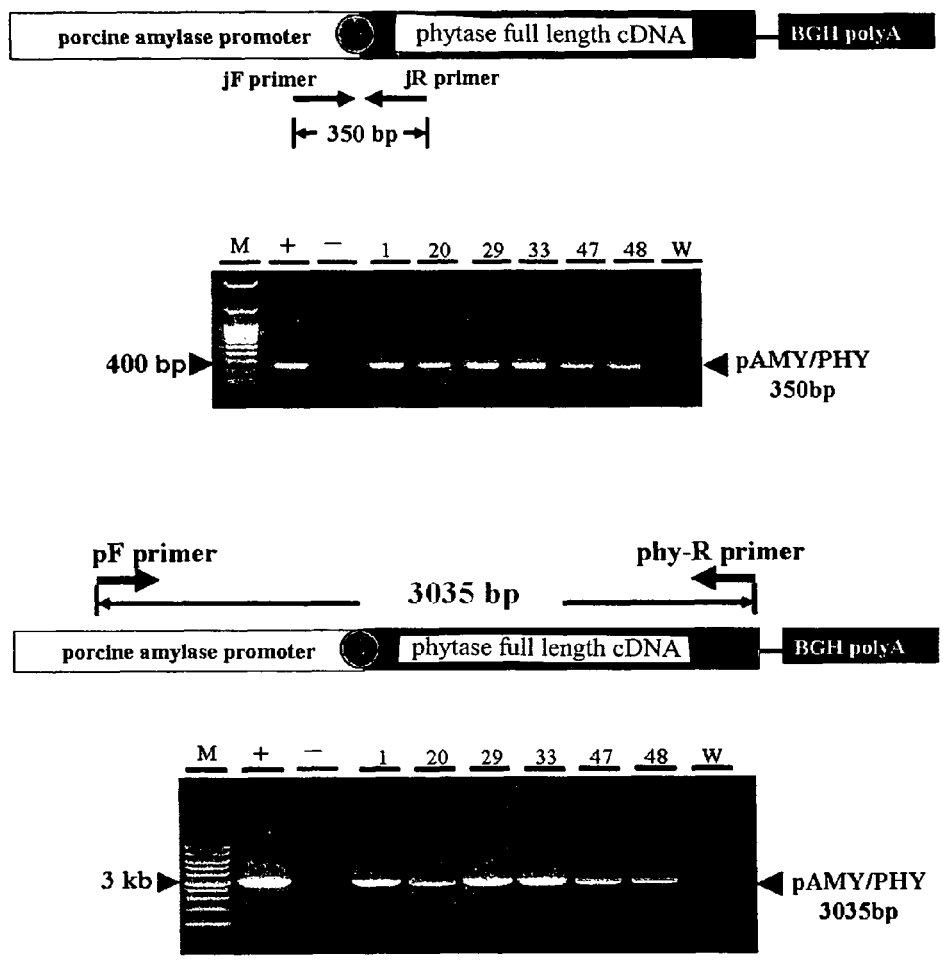
FIG. 3 shows the results of PCR verification of transgenic mice harboring the phytase transgene. "M" denotes markers; "+" denotes positive control; "−" denotes negative control; and "W" denotes wildtype. The numbers correspond to the identification numbers of the transgenic mice.

The results of the PCR analysis are shown in FIGS. 2 and 3. As can be seen from the results, pups No. 4, 29, 33 and 48 carry the cellulase transgene (FIG. 2), while pups No. 1, 20, 29, 33, 47 and 48 carry the phytase transgene (FIG. 3), which means that pups No. 29, 33 and 48 carry both transgenes. The identities of the transgenes were further confirmed by PCR using primer pair 1216C-jF+1216C-jR or 1216P-jF+1216P-jR.

TABLE 3

Primers Used in Transgenic Animal DNA Analysis

| Primer | Sequence | Tm value (° C.) | PCR Product |
|---|---|---|---|
| 1216-pF | AGGGACCGAAGGAGAGTGTT (SEQ ID NO: 19) | 64.1 | 314 bp |
| 1216-pR | ACCATTCTTGCTCTGCTGTGA (SEQ ID NO: 20) | 64.6 | |
| 1216C-jF | ACCGTTGACAACCTCAGAGCA (SEQ ID NO: 21) | 66.8 | 404 bp |
| 1216C-jR | TCGTTCACCAAAGTGTCCAGA (SEQ ID NO: 22) | 65.2 | |
| 1216C-aF | CATTGTTGCAGCCTTACAA (SEQ ID NO: 23) | 59.0 | 262 bp |
| 1216C-aR | ACTCAGACAATGCGATGCA (SEQ ID NO: 24) | 60.8 | |
| 1216P-jF | ACCGTTGACAACCTCAGAGCAA (SEQ ID NO: 25) | 68.8 | 350 bp |
| 1216P-jR | ACGCTCGTCGACATCAGCAATA (SEQ ID NO: 26) | 70.0 | |

TABLE 3-continued

Primers Used in Transgenic Animal DNA Analysis

| Primer | Sequence | Tm value (° C.) | PCR Product |
|---|---|---|---|
| 1216P-aF | TCGGCTAAGCGATAACAG (SEQ ID NO: 27) | 58.4 | 291 bp |
| 1216P-aR | ACAACAGATGGCTGGCAACT (SEQ ID NO: 28) | 64.1 | |
| CEL-R | GGATCCTTATTCCTTTGGTTTTC (SEQ ID NO: 29) | 53.8 | |
| PHY-R | GGATCCTTACAAACTGCACGCCGG (SEQ ID NO: 30) | 64.5 | |
| CEL-Hyb-3' | TCCGTTCCATTCAACTGGTG (SEQ ID NO: 31) | 65.2 | |
| PHY-Hyb-3' | TCAGTCACGTTCGCGTTATCT (SEQ ID NO: 32) | 65.0 | |

Example 6 Production of Transgenic Pigs

Sexually mature crossbred gilts (more than 6 month old) were used in the present study as embryo donors and recipients. Superovulated donor gilts were artificially inseminated and fertilized embryos were surgically recovered from their oviducts. The embryos were centrifuged at 12,000× g for 10 minutes at 25° C. in order to show the pronuclei (the cytoplasm of porcine embryos was opaque with lipid and pronuclei were invisible before centrifugation).

Microinjection of the embryos was performed as described above in Example 4. Embryos surviving the microinjection process as judged by morphological observation were implanted into oestrous recipient gilts. About 10 to 20 microinjected porcine embryos were transferred into each of the two oviducts of recipient gilts. Embryos were allowed to come to term and the newborn pigs were analyzed for the presence of the transgenes by PCR and Southern blot as described below.

In the present study, 145 porcine embryos were microinjected with the transgenes, among which 138 surviving embryos were implanted into the oviducts of 6 recipient gilts. Among the 6 recipients, 2 were pregnant and gave birth to a total of 13 piglets.

Example 7 Analysis of Transgenic Pig Genomic DNA

Genomic DNA was obtained from tissue samples removed from the ears of the 13 potential transgenic piglets by the same procedures as described in Example 5. PCR was performed on the genomic DNA samples using one of the following primer pairs: 1216-pF+1216C-aR (for full-length cellulase transgene), 1216-pF+1216P-aR (for full-length phytase transgene), 1216C-jF+1216C-jR (for promoter-cellulase junction) and 1216P-jF+1216P-jR (for promoter-phytase junction) (see Table 3).

Figure 4A:
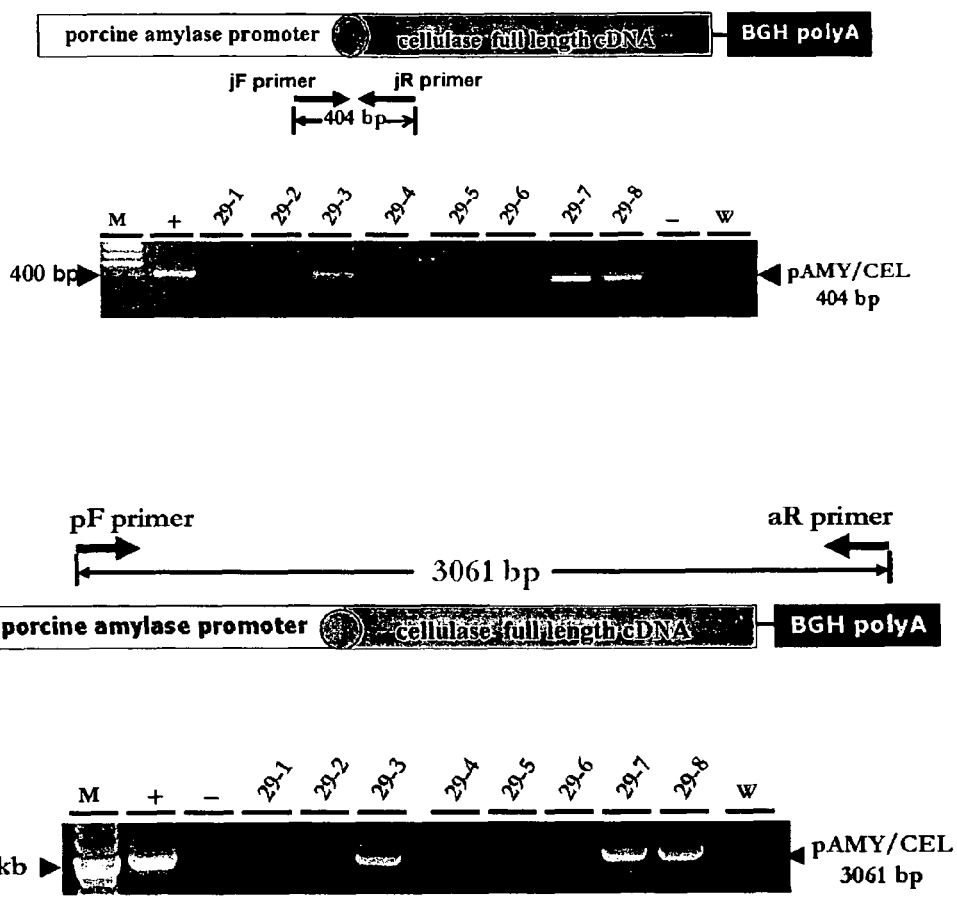
FIGS. 4A and 4B show the results of PCR verification of transgenic pigs harboring the cellulase transgene. "M" denotes markers; "+" denotes positive control; "−" denotes negative control; and "W" denotes wildtype. The numbers correspond to the identification numbers of the transgenic pigs.
Figure 4B:
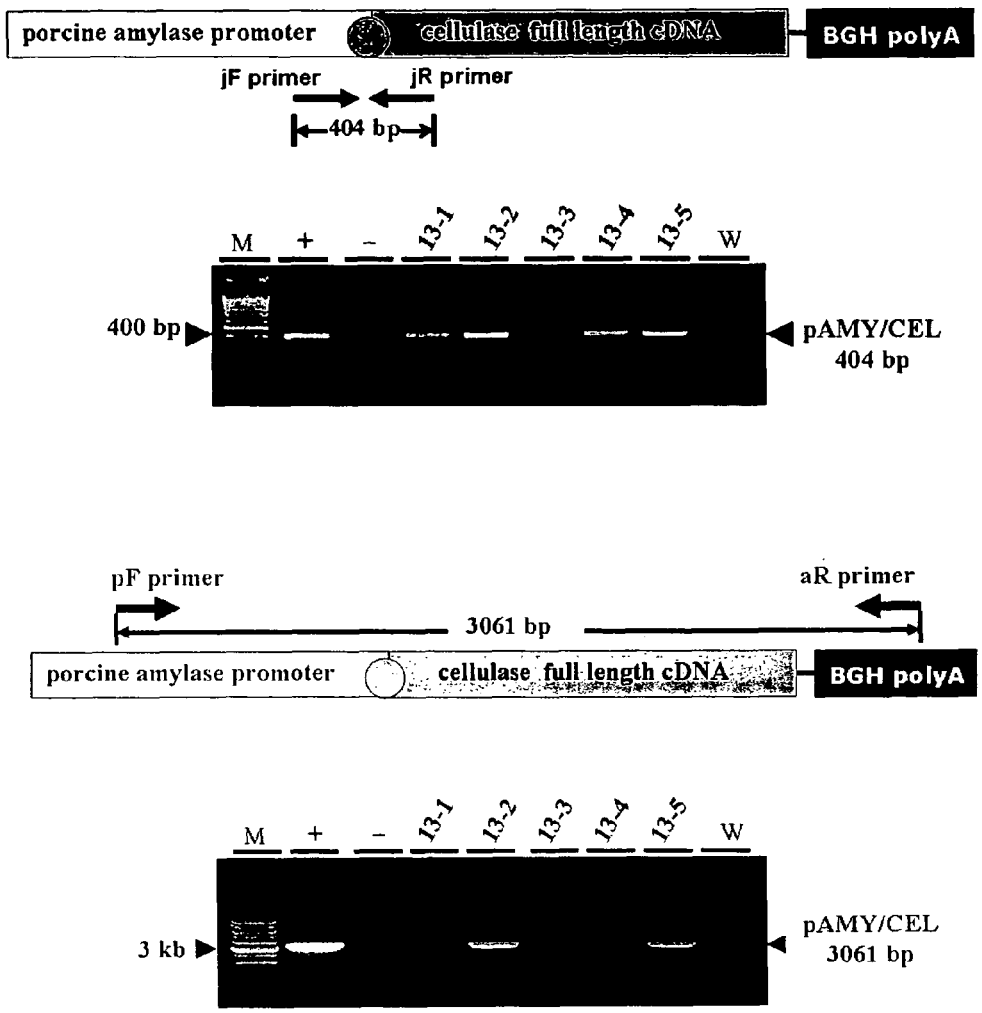
Figure 5:
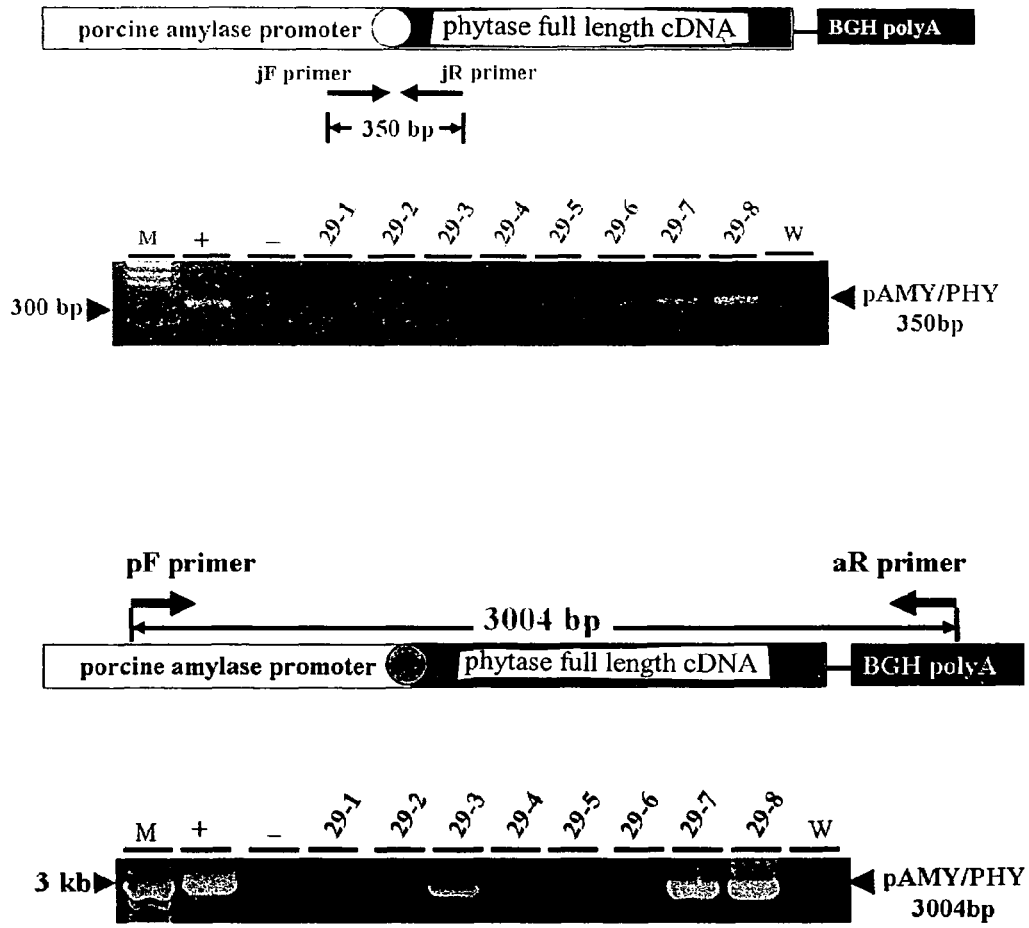
FIG. 5 shows the results of PCR verification of transgenic pigs harboring the phytase transgene. "M" denotes markers; "+" denotes positive control; "−" denotes negative control; and "W" denotes wildtype. The numbers correspond to the identification numbers of the transgenic pigs.

The results of the PCR analysis are shown in FIGS. 4 and 5. As can be seen from the results, piglets No. 29-3, 29-7, 29-8, (FIG. 4A) and 13-2 and 13-5 (FIG. 4B) carry the cellulase transgene, while piglets No. 29-7 and 29-8 carry the phytase transgene (FIG. 5), which means that piglets No. 29-7 and 29-8 carry both transgenes. Among the 5 transgenic piglets, piglet No. 13-2 died of bacterial infection 10 days after birth.

Southern blotting was performed on the genomic DNA of the 5 transgenic piglets in order to understand the level of integration of the transgenes, using PCR products of primer pairs 1216C-aF+1216C-aR, 1216P-aF+1216P-aR, CEL-BamHI-5'+CEL-Hyb-3' and PHY-BamHI-5'+PHY-Hyb-3' (see Tables 2 and 3) as probes. Recovered and purified PCR products were first denatured in boiling water and placed on ice. Radioactive labeling of the PCR products was carried out with Rediprime™ II DNA Labeling System (GE Healthcare UK Ltd, UK) according to the manufacturer's instructions. Southern Blotting was performed essentially as described in Koetsier et al., 1993, Biotechniques 15(2):260-2 (hereby incorporated herein by reference). The procedures employed are outlined below.

Genomic DNA of the 5 transgenic piglets digested with relevant restriction enzymes was subjected to 0.8% agarose gel electrophoresis (50V, 4-6 hrs) and depurination with 0.25 N HCl for 15 minutes. After the Bromophenol Blue dye turned yellow, the gel slab was incubated in a denaturing solution containing 1.5 M NaCl and 0.4 N NaOH. After blotting for 2.5 to 4 hours, the nylon membrane (Hybond™-N+, GE Healthcare UK Ltd) with DNA blots was placed into a 2×SSC solution for neutralizing the reaction. For pre-hybridization, the membrane was incubated in a pre-hybridization solution (2×SSC, 1% SDS, 0.5% fat-free milk powder and 0.75 mg/ml denatured salmon sperm DNA) at 66° C. for 2 to 5 hours. For hybridization, the membrane was moved into a hybridization solution (2×SSC, 1% SDS, 0.5% fat-free milk powder, 0.5 mg/ml denatured salmon sperm DNA and 10% dextran sulfate) containing the radioactive labeled probes, and incubated at 66° C. for 16 to 24 hours. After hybridization, the membrane was twice washed at 55° C. for 20 minutes with a solution containing 0.1% SDS and 0.1×SSC. Finally, the membrane was air dried and analyzeded by a Bio-imaging Analyzer (BAS-1500, FUJIFILM, Japan).

Figure 6:
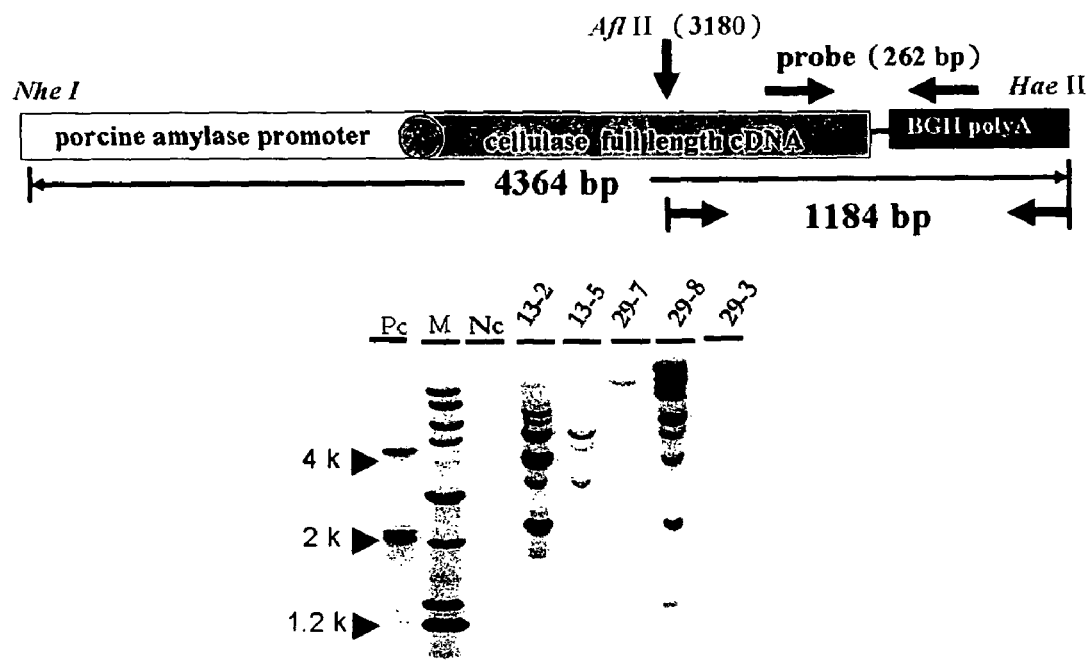
FIG. 6 shows the results of Southern Blot analysis of transgenic pigs harboring the cellulase transgene, wherein the porcine genomic DNA was digested with Afl II. "M" denotes markers; "Pc" denotes positive control; and "Nc" denotes negative control. The numbers correspond to the identification numbers of the transgenic pigs.
Figure 7:
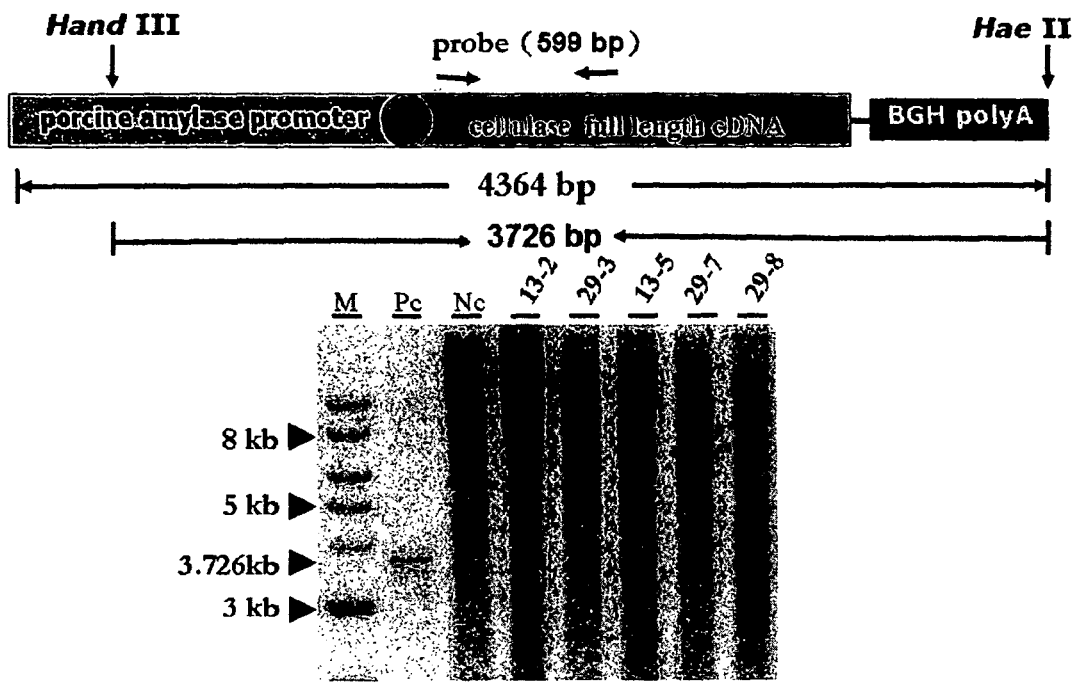
FIG. 7 shows the results of Southern Blot analysis of transgenic pigs harboring the cellulase transgene, wherein the porcine genomic DNA was double digested with Hind III and HaeII. "M" denotes markers; "Pc" denotes positive control; and "Nc" denotes negative control. The numbers correspond to the identification numbers of the transgenic pigs.
Figure 8:
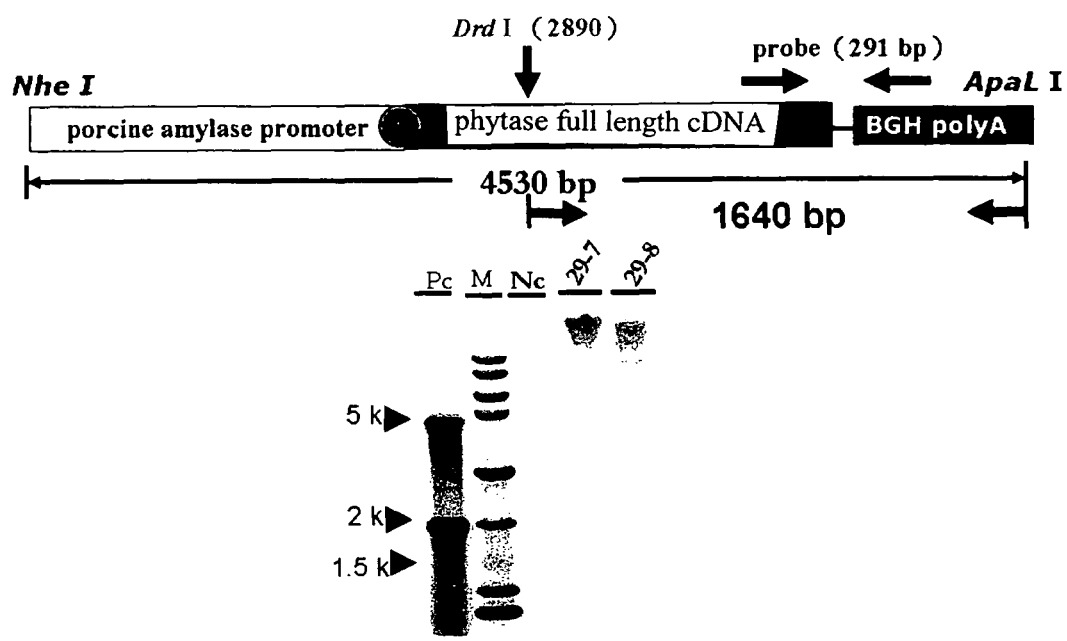
FIG. 8 shows the results of Southern Blot analysis of transgenic pigs harboring the phytase transgene, wherein the porcine genomic DNA was digested with Drd I. "M" denotes markers; "Pc" denotes positive control; and "Nc" denotes negative control. The numbers correspond to the identification numbers of the transgenic pigs.
Figure 9:
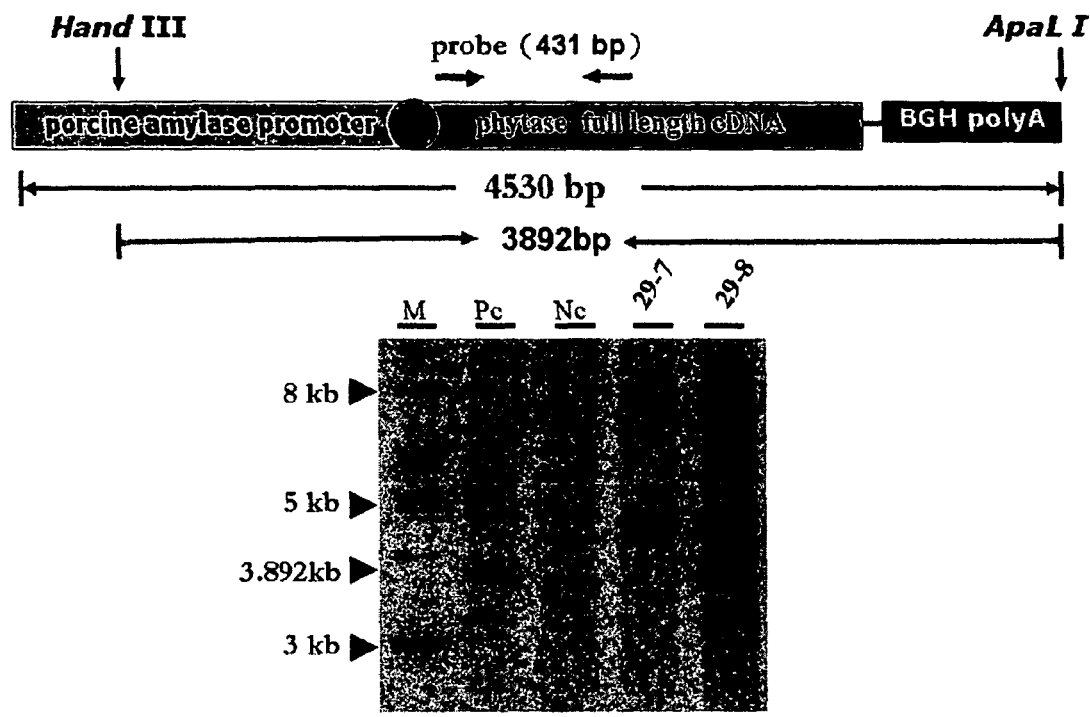
FIG. 9 shows the results of Southern Blot analysis of transgenic pigs harboring the phytase transgene, wherein the porcine genomic DNA was double digested with Hind III and ApaL I. "M" denotes markers; "Pc" denotes positive control; and "Nc" denotes negative control. The numbers correspond to the identification numbers of the transgenic pigs.

The results of the Southern Blot analysis are shown in FIGS. 6 to 9. In FIG. 6, the porcine genomic DNA was digested with Afl II and the probe was the PCR product of primer pair 1216C-aF+1216C-aR. The image shows that all of the 5 transgenic piglets carry the cellulase transgene, but integrated copy numbers may be larger in piglets No. 13-2 and 29-8 in view of the stronger hybridization signals for the two. In FIG. 7, the porcine genomic DNA was double digested with Hind III and Hae II and the probe was the PCR product of primer pair CEL-BamHI-5'+CEL-Hyb-3'. The image shows that except for piglet No. 13-2 (whose genomic DNA was damaged), the other four piglets all have the 3,726-kb fragment same as the positive control, meaning that they all carry the cellulase transgene but with different integration levels. In FIG. 8, the porcine genomic DNA was digested with Drd I and the probe was the PCR product of primer pair 1216P-aF+1216P-aR. The image shows that piglet No. 29-8 carries the phytase transgene, but the restriction digestion for piglet No. 29-7 seems insufficient. In FIG. 9, the porcine genomic DNA was double digested with Hind III and ApaL I and the probe was the PCR product of primer pair PHY-BamHI-5'+PHY-Hyb-3'. As can be seen from the image, only piglet No. 29-8 has the 3,892-kb fragment same as the positive control. However, piglet No. 29-7 has a fragment near the 8 kb position, which is believed to represent the undigested phytase transgene.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An isolated DNA promoter comprising the nucleotide sequence of SEQ ID NO:1.

2. A recombinant DNA construct comprising the promoter according to claim 1 operatively linked to a nucleotide sequence of interest.

3. The recombinant DNA construct according to claim 2, wherein the nucleotide sequence of interest is a coding sequence.

4. The recombinant DNA construct according to claim 3, wherein the nucleotide sequence of interest encodes a digestive enzyme.

5. The recombinant DNA construct according to claim 4, wherein the digestive enzyme is selected from the group consisting of a phytases, a cellulases, a glucanase and a xylanase.

6. The recombinant DNA construct according to claim 2, comprising the nucleotide sequence of SEQ ID NO: 2.

7. A method for producing a transgenic pig that exhibits enhanced digestion of cellulose, comprising the steps of (a) providing a pig embryo, (b) introducing into the pig embryo by pronuclear microinjection a transgene including a promoter comprising the nucleotide sequence of SEQ ID NO:1 operatively linked to the nucleotide sequence of SEQ ID NO:2, (c) inserting the pig embryo into a pseudopregnant pig, (d) allowing the pig embryo to develop to term, thereby producing a transgenic pig, and (e) identifying the transgenic pig from step (d) whose genome comprises the transgene.

8. A transgenic pig whose genome comprises a transgene including a promoter comprising the nucleotide sequence of SEQ ID NO:1 operatively linked to the nucleotide sequence of SEQ ID NO:2, wherein the transgenic pig exhibits enhanced digestion of cellulose.

9. The recombinant DNA construct according to claim 6, further comprising the nucleotide sequence of SEQ ID NO: 4.

10. The method according to claim 7, wherein the transgene further comprises the nucleotide sequence of SEQ ID NO:4.

11. The transgenic pig according to claim 8, wherein the transgene further comprises the nucleotide sequence of SEQ ID NO: 4.

* * * * *